United States Patent [19]

Armstrong

[11] 4,238,188

[45] * Dec. 9, 1980

[54] EXTRAORAL FORCE-APPLYING ORTHODONTIC APPLIANCE

[75] Inventor: Maclay M. Armstrong, Seattle, Wash.

[73] Assignee: Northwest Orthodontics, Inc., Seattle, Wash.

[ * ] Notice: The portion of the term of this patent subsequent to Sep. 26, 1995, has been disclaimed.

[21] Appl. No.: 21,571

[22] Filed: Mar. 19, 1979

Related U.S. Application Data

[63] Continuation-in-part of Ser. No. 655,401, Feb. 5, 1976, Pat. No. 4,155,161, which is a continuation-in-part of Ser. No. 613,243, Sep. 15, 1975, abandoned.

[51] Int. Cl.² ............................................. A61C 7/00
[52] U.S. Cl. ................................................. 433/5
[58] Field of Search ...................................... 433/5

[56] References Cited

U.S. PATENT DOCUMENTS

| | | | |
|---|---|---|---|
| 3,526,035 | 9/1970 | Armstrong | 433/5 |
| 3,772,789 | 11/1973 | DeWoskin | 433/5 |

*Primary Examiner*—Robert Peshock

*Attorney, Agent, or Firm*—Robert W. Beach; Ward Brown

[57] ABSTRACT

An extraoral force-reaction device engageable with the wearer's head and/or neck, such as a headcap or a neckband, is connected to an intraoral force-applying device, such as molar bands, by force-producing means, such as springs. Snapback of the force-applying means is controlled in response to relative movement of the intraoral means and the extraoral force-reaction means away from each other beyond a predetermined maximum limit, or in response to stressing of the force-producing means beyond a predetermined maximum degree of force exerted by the force-producing means. Snapback control may be effected by latching of a limit latch to prevent or limit return movement of the force-reaction device and the force-applying device, or disconnectible means can be disconnected to interrupt the application of primary force to the intraoral means and reaction force to the head or neck engageable means. The force to be exerted by the spring force-producing means can be readily adjustable in predetermined increments, such as by engagement of different holes in a spring anchor strap with an anchor pin, or by a linear ratchet device. Also, various components of the extraoral force-reaction device can be assembled and adjusted as to length by connection of separable connections, which may include linear ratchet means.

10 Claims, 69 Drawing Figures

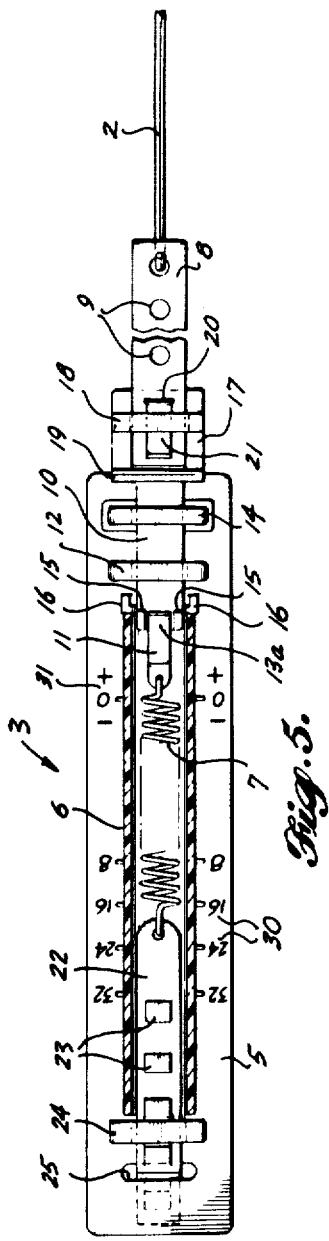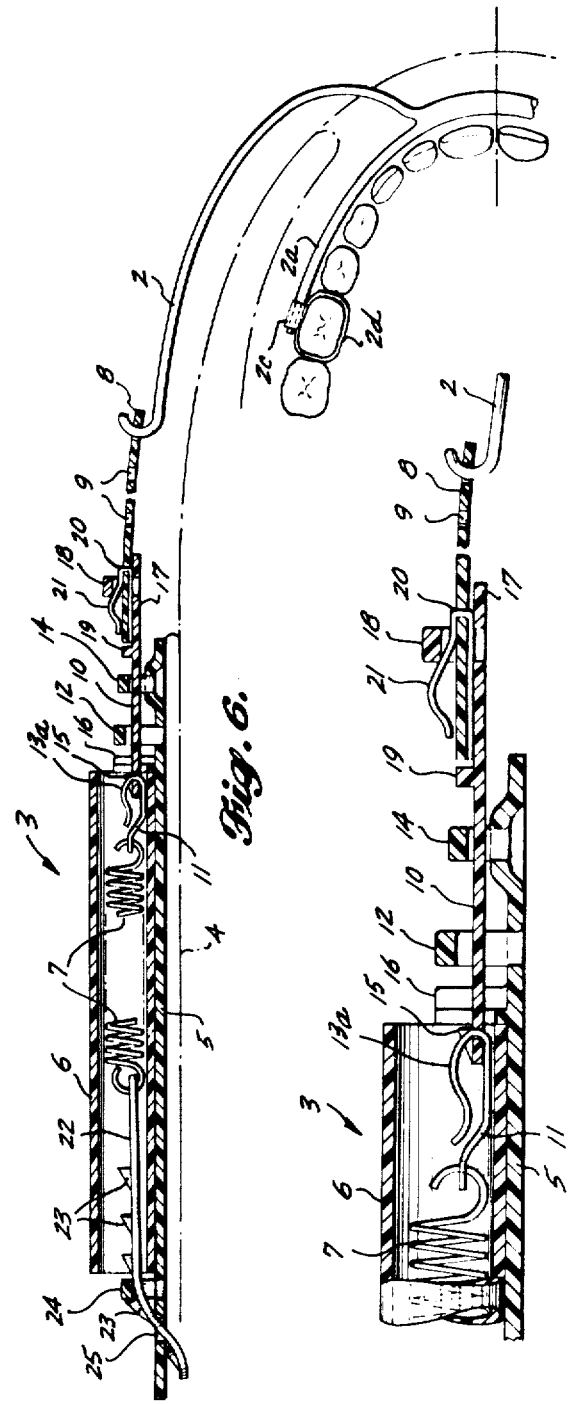

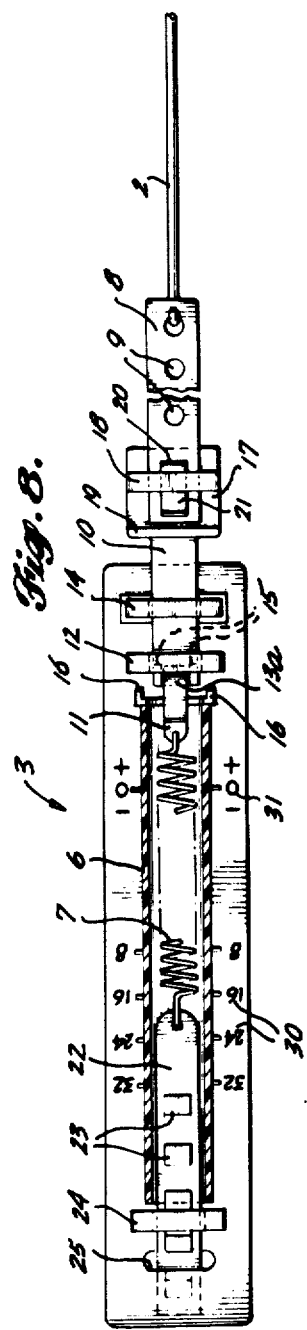
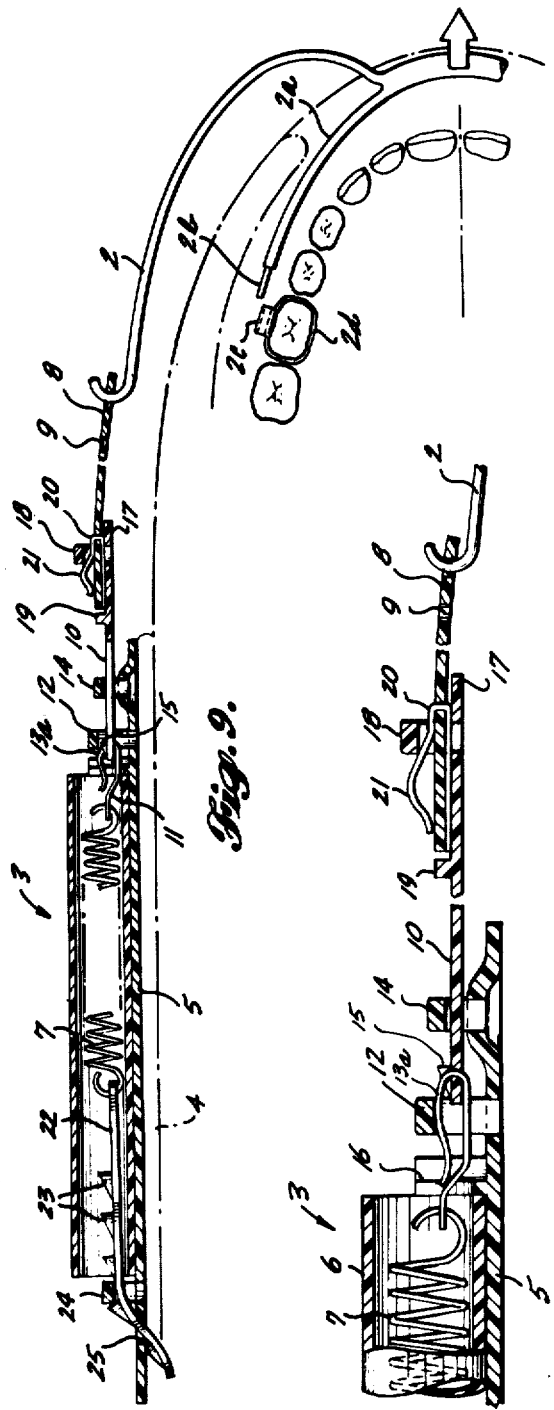
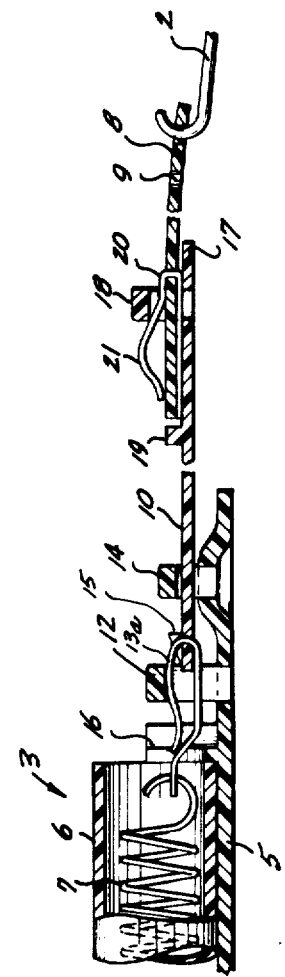

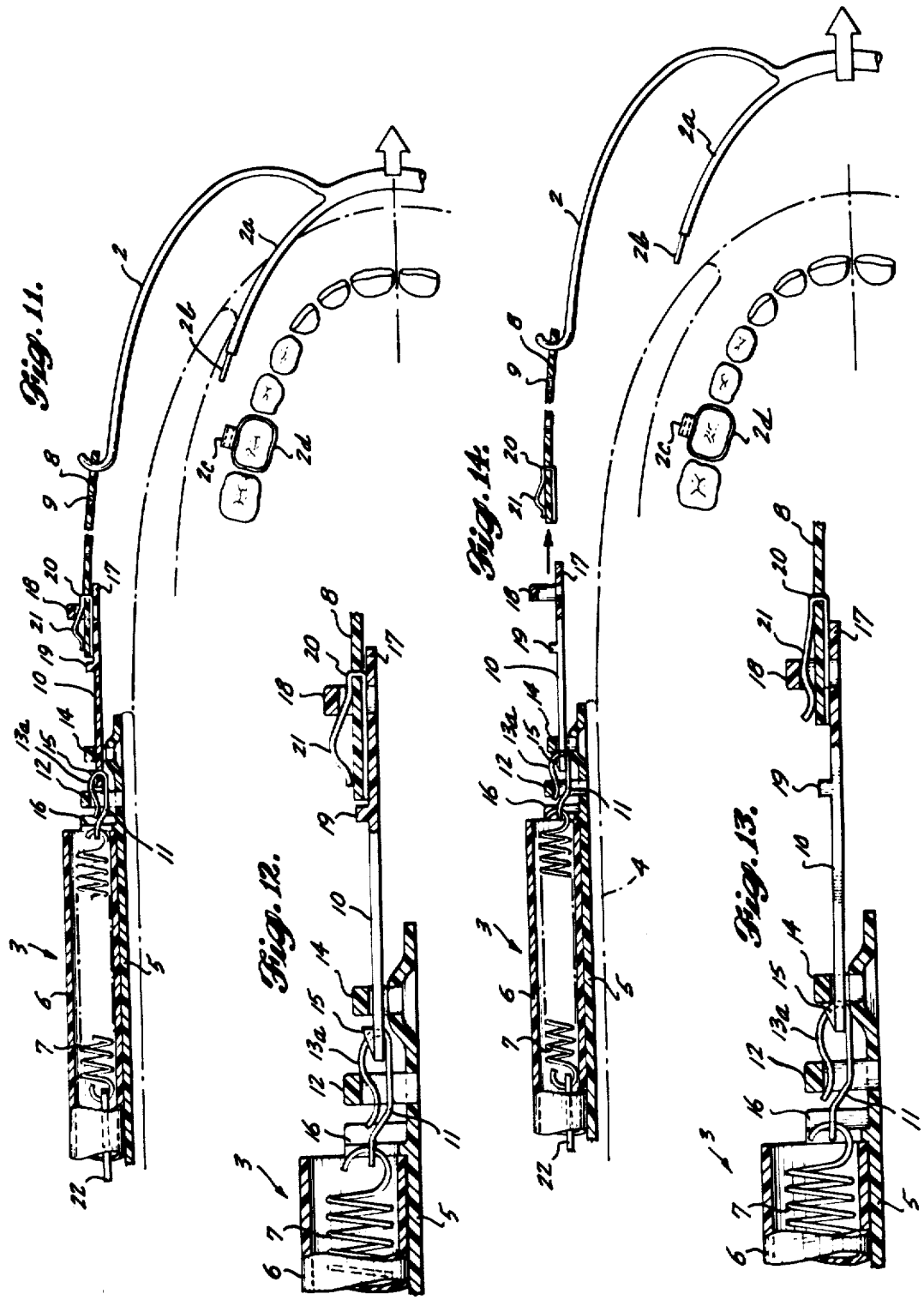

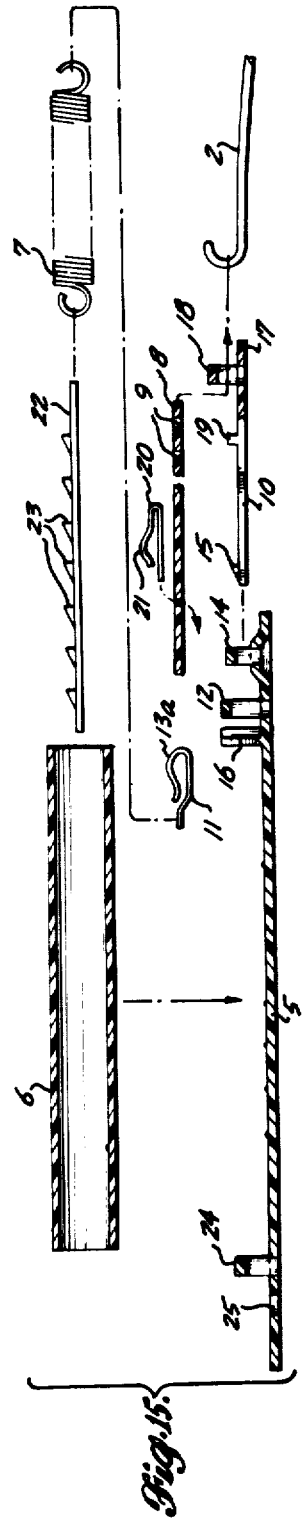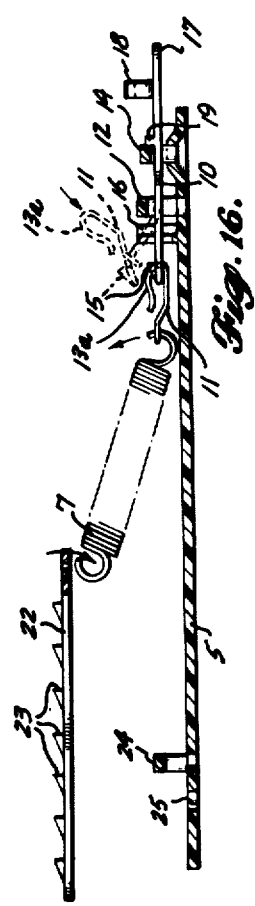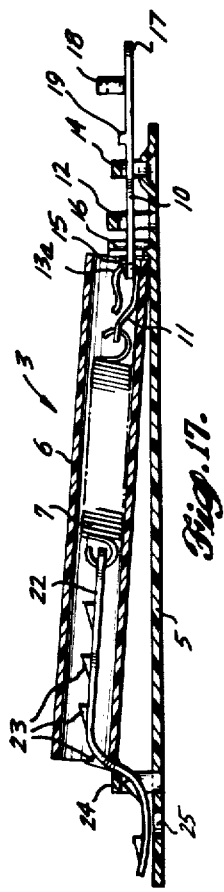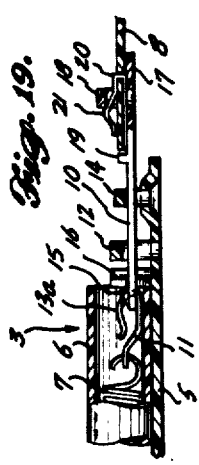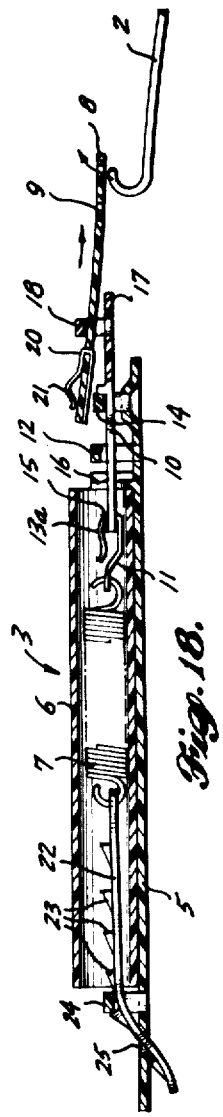

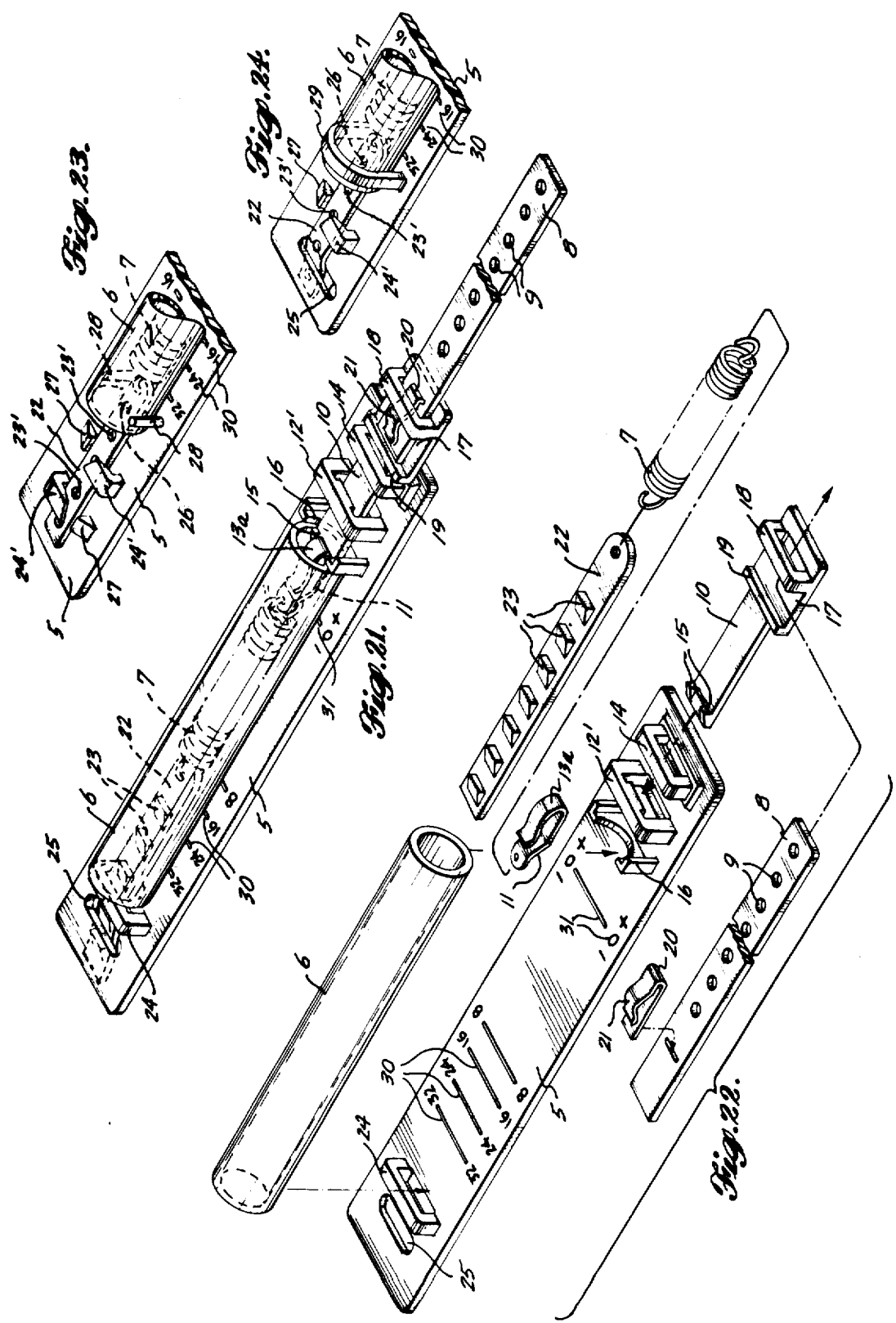

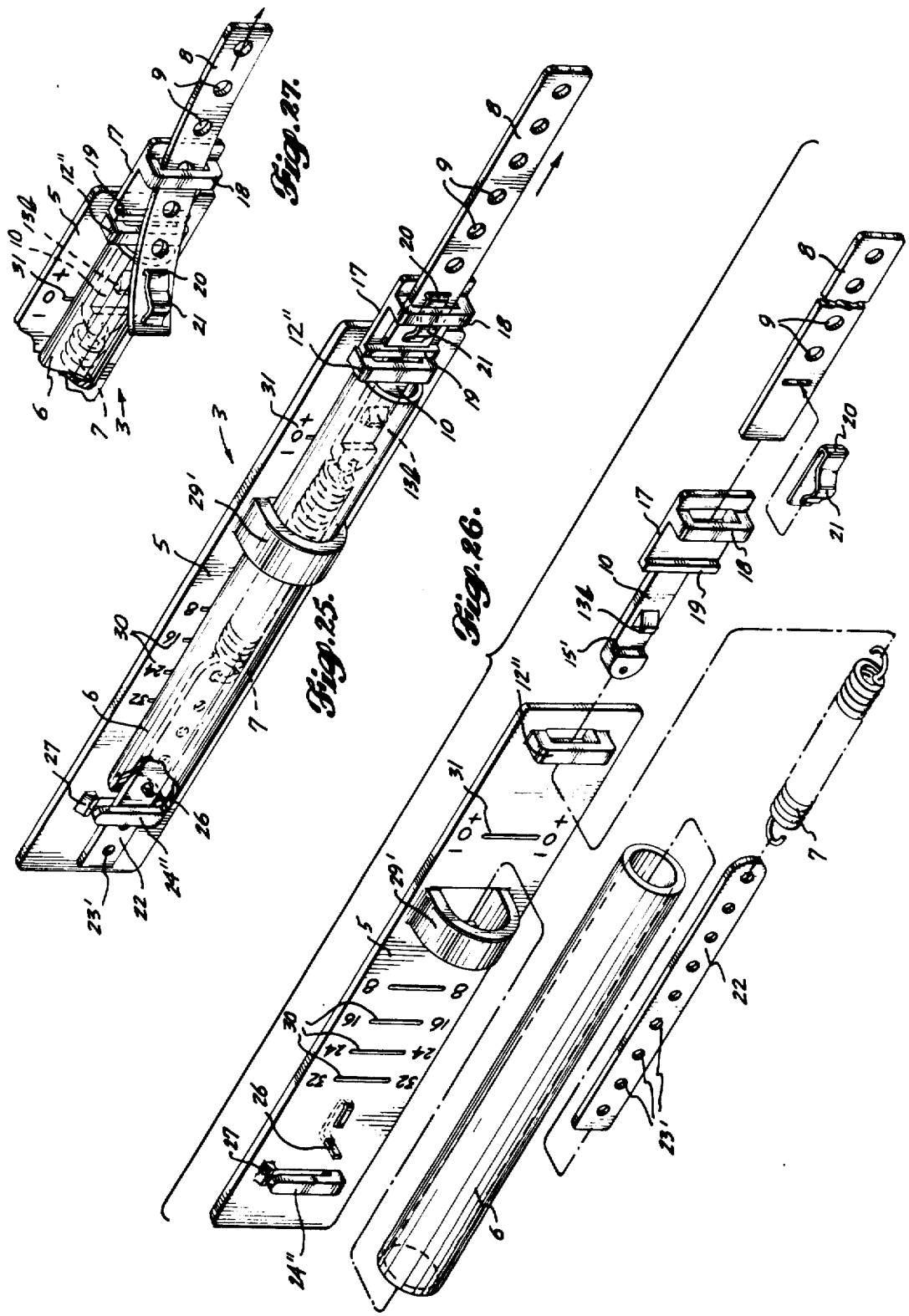

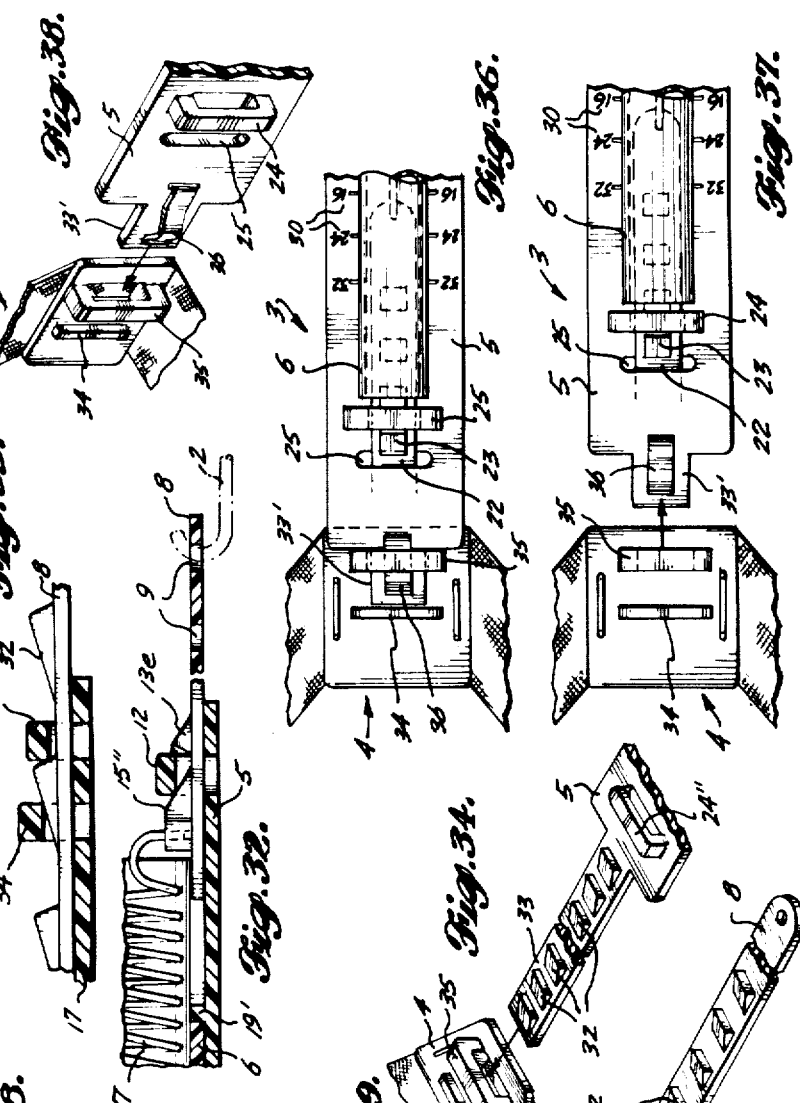
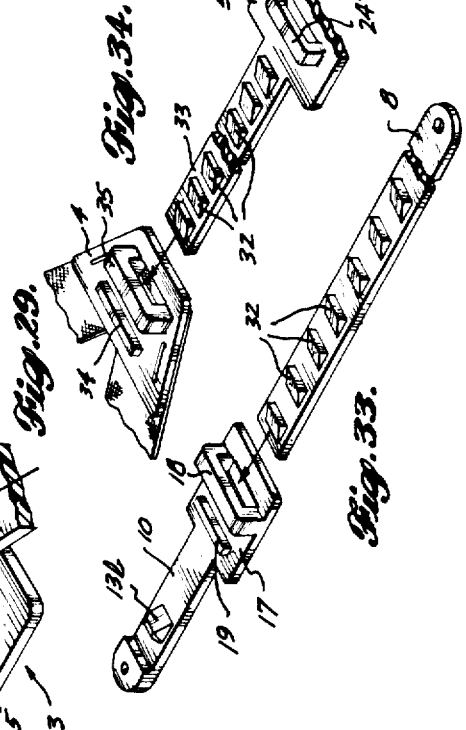
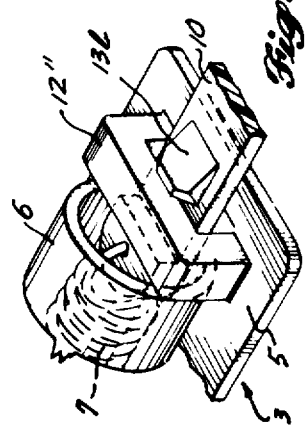
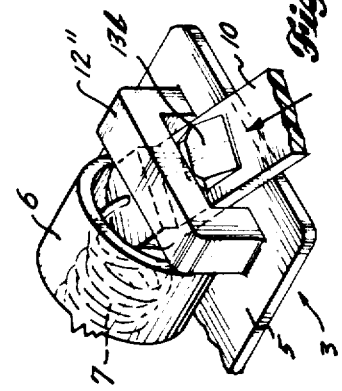

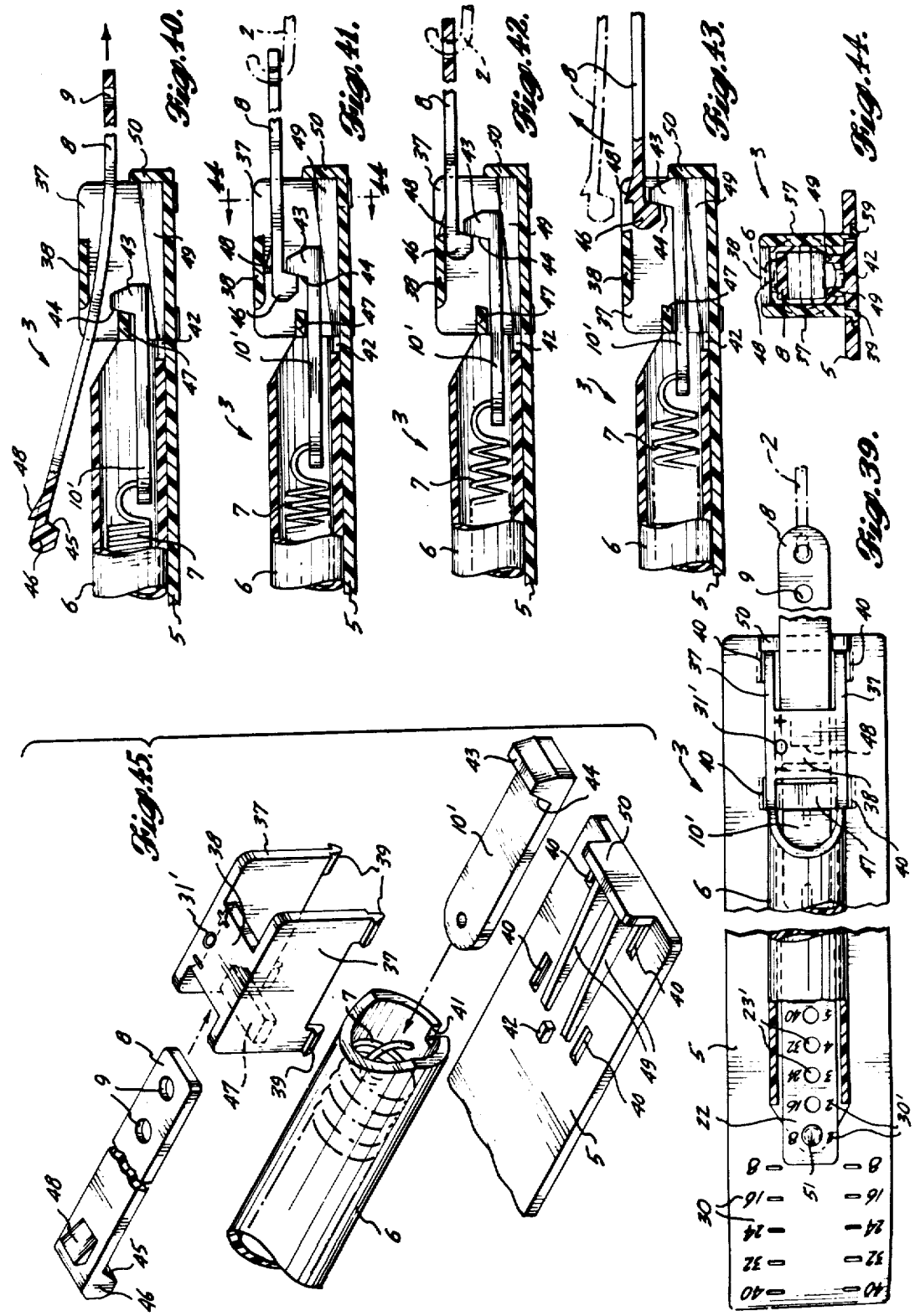

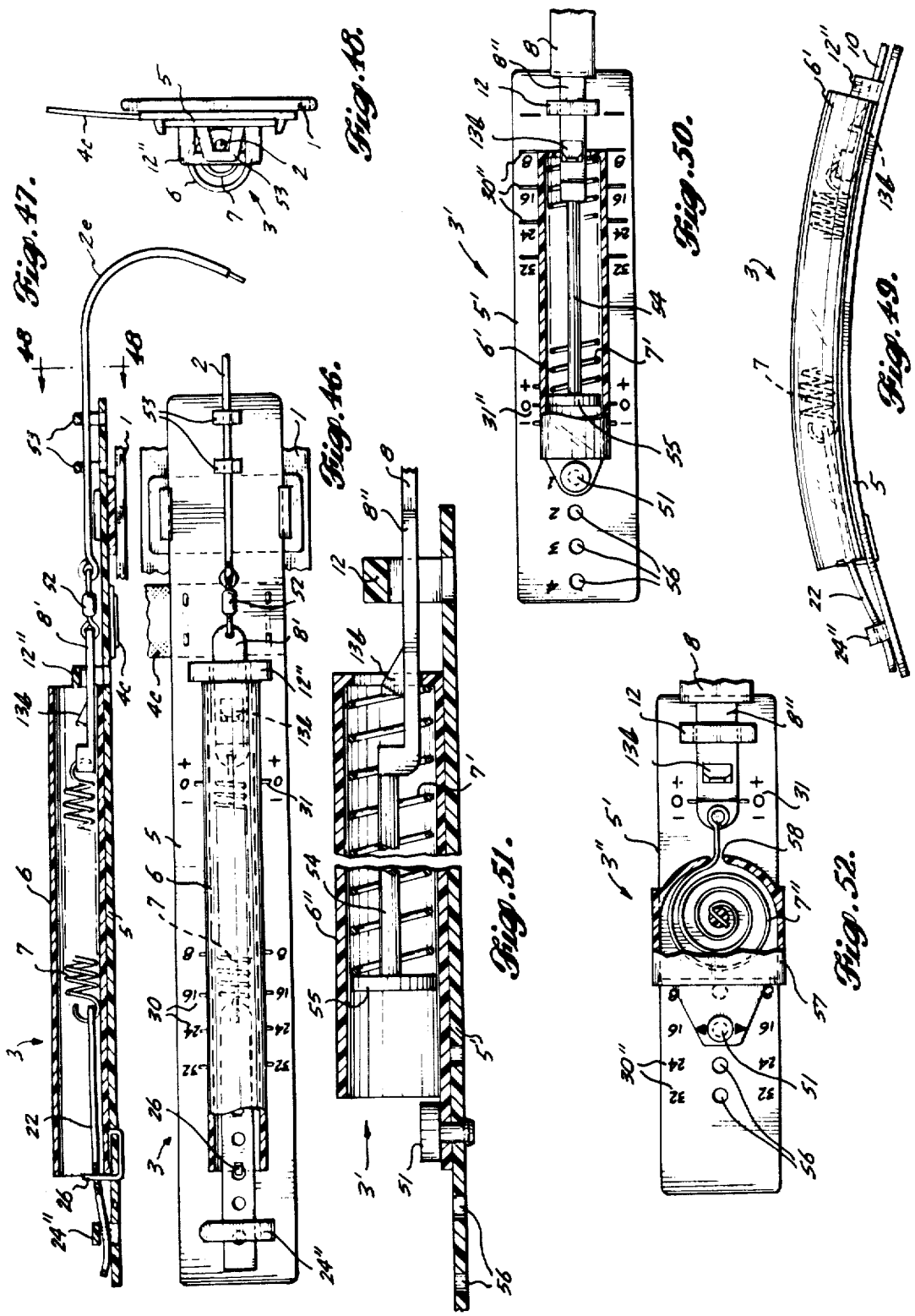

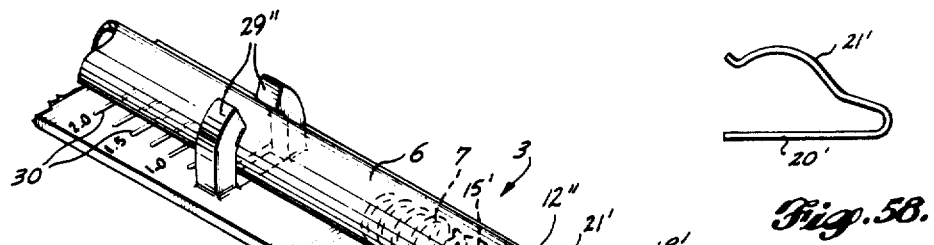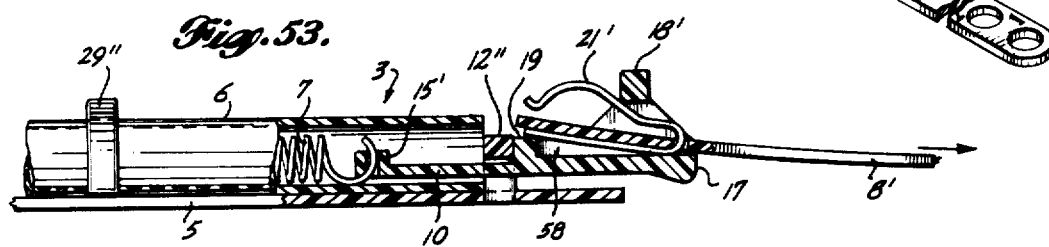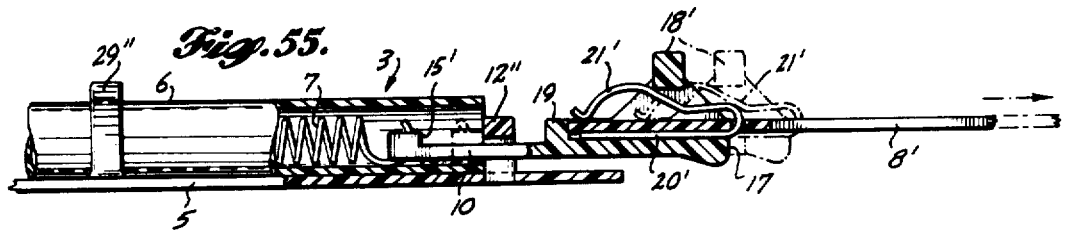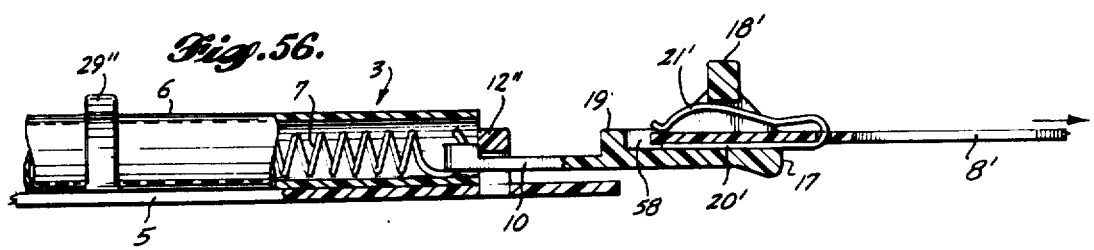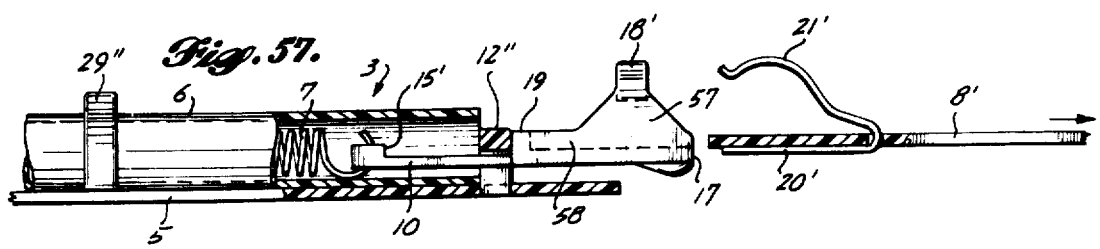

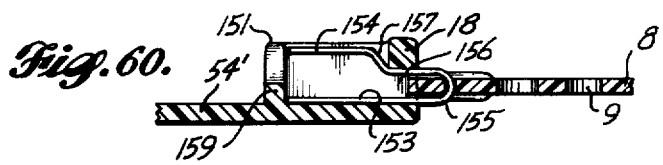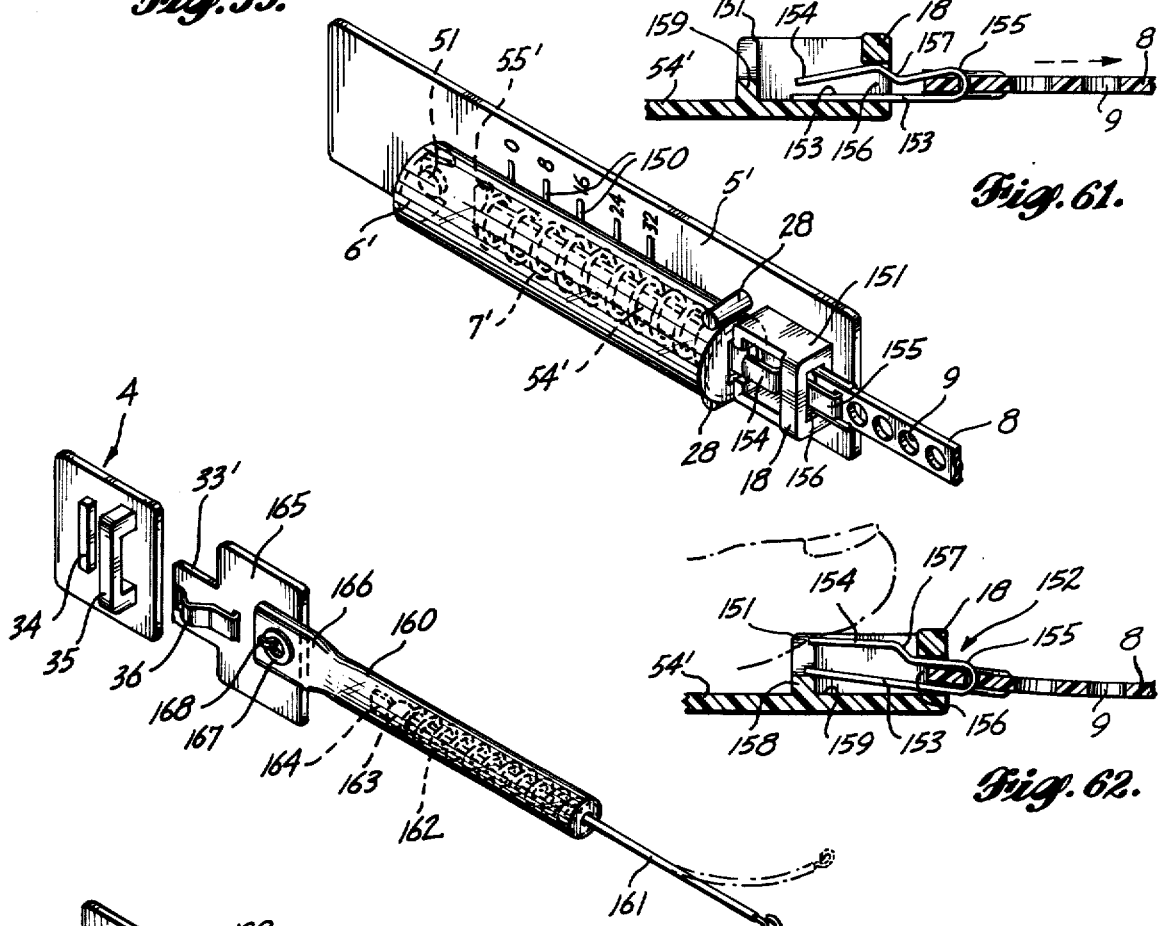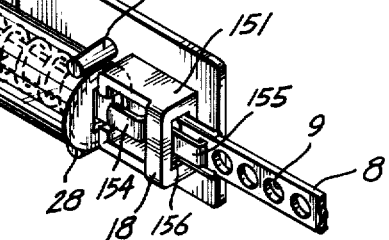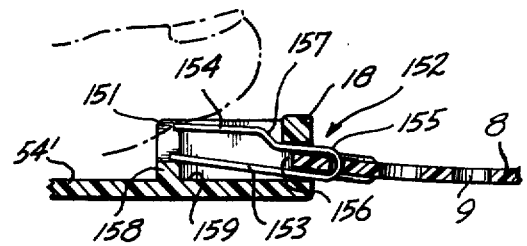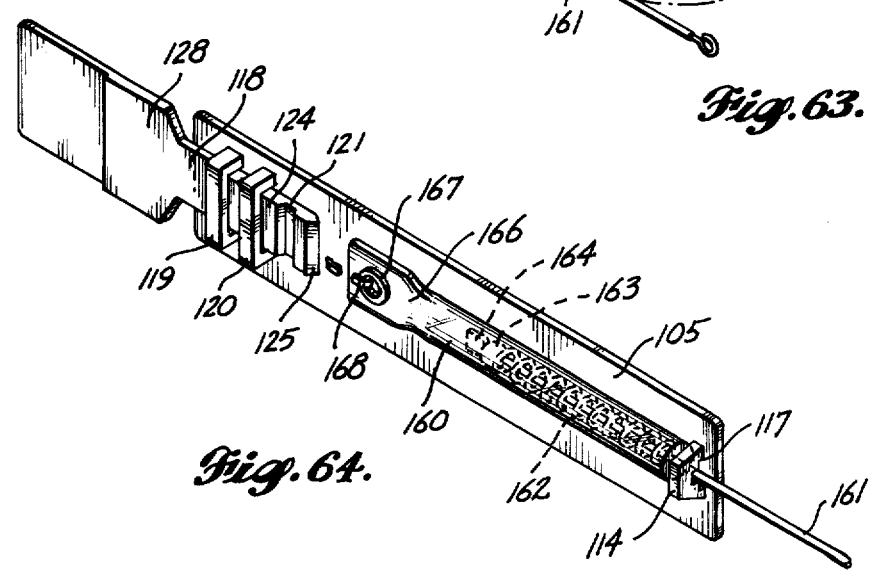

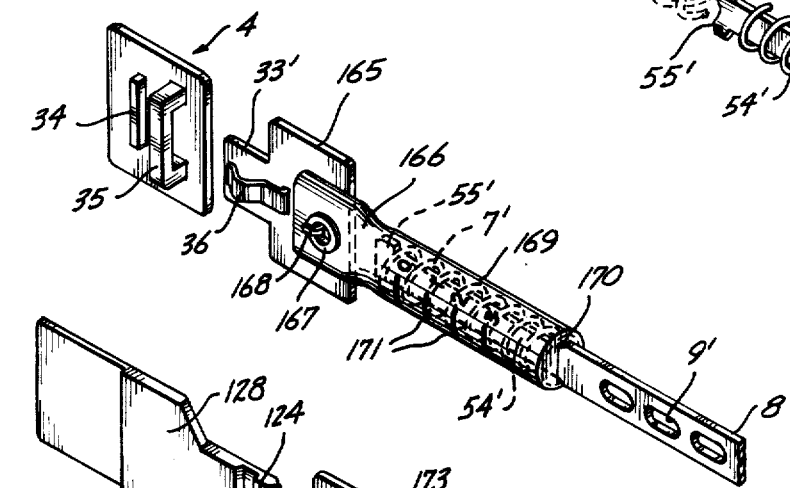
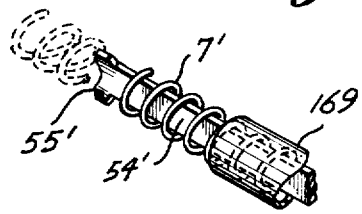
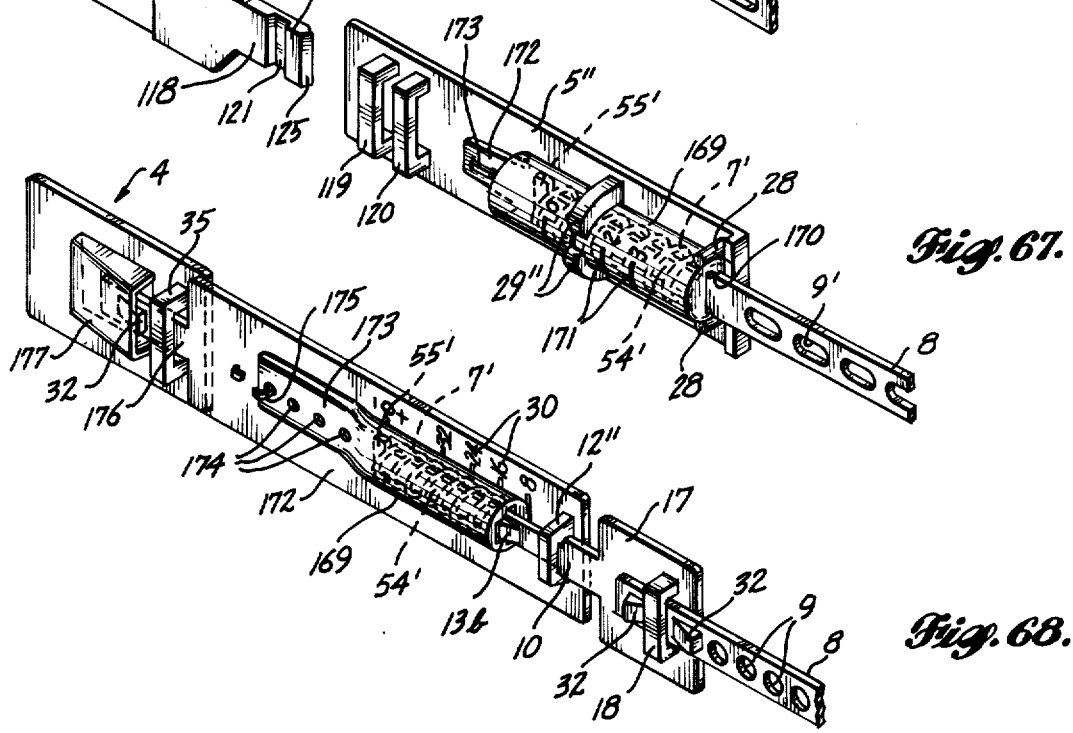
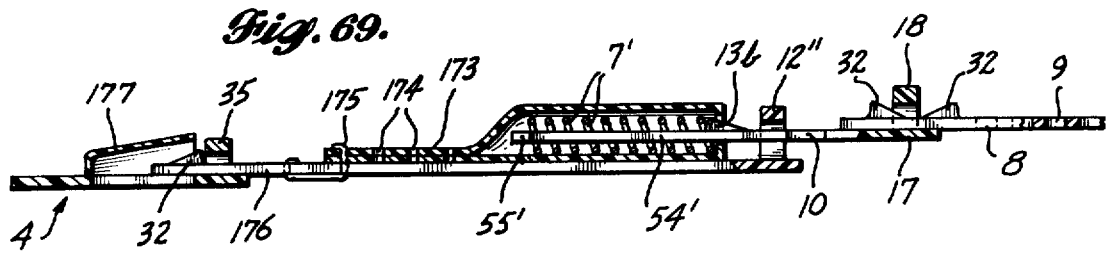

EXTRAORAL FORCE-APPLYING ORTHODONTIC APPLIANCE

CROSS-REFERENCE

This application is a continuation-in-part of my application Ser. No. 655,401, filed Feb. 5, 1976 now U.S. Pat. No. 4,155,161 issued May 22, 1979, for Extraoral Force-Applying Orthodontic Appliance, which is a continuation-in-part of my application Ser. No. 613,243, filed Sept. 15, 1975 and now abandoned, for Extraoral Force-Applying Orthodontic Appliance.

BACKGROUND OF THE INVENTION

1. Field of the Invention

This application relates to orthodontic appliances capable of applying a primary force to a jaw, the reaction from which force is applied to the exterior of the head and/or neck by an extraoral force-reaction device.

2. Prior Art

A device for applying primary force to a jaw by an intraoral device and exerting the reaction force on an extraoral force-reaction device engageable with the wearer's head or neck is shown, for example, in the Armstrong U.S. Pat. No. 3,526,035. The appliance of the present invention constitutes an improvement over the apparatus shown in that patent. A device for applying a force to an intraoral device utilizing a compression spring is shown in DeWoskin U.S. Pat. No. 3,772,789.

3. The Problem

The problem which has not been solved by prior orthodontic devices has been provision of protection against injury by snapback of the intraoral device should the intraoral device be pulled from the patient's mouth and released while it is still connected to the force-producing unit, or even if the tips of such device were merely disengaged from their tooth band sockets and the device then released while such tips are still in the mouth. Such snapback could occur by a patient improperly removing the device, or by childish pranks, or by a part of the headgear being caught by either a stationary or a moving object. This problem has been recognized as discussed in Snead U.S. Pat. 3,903,604 at column 1, lines 21 to 31, for example. Even if the tips of such device were not pulled from the tooth band sockets a yank on the headgear resulting from such catching would cause discomfort and possible injury.

SUMMARY OF THE INVENTION

A principal object of the present invention is to provide effective control over the snapback of a force-producing unit applying a sustained yieldable force to a jaw such as by intraoral gear used in orthodontic treatment. More specifically, it is an object to exercise such snapback control when extraoral force-reaction gear engageable with the wearer's head and/or neck and force-applying gear are separated more than a predetermined amount, or a force is exerted between such gear components of more than a predetermined magnitude.

A further object is to provide such control over the force-producing means without appreciably restricting the excursions of which the lower jaw and head are capable.

If normal corrective force-applying operation of the gear is interrupted by control action on the force-producing unit, it is an object to enable the gear to be rearranged or restored to its operative condition quickly and easily.

Another object is to provide in an orthodontic appliance having extraoral force-reaction and intraoral force-applying components a force-producing unit which will produce a sustained, substantially constant, predetermined force on a jaw, such as by a preliminarily stressed spring, which force-producing unit can be adjusted quickly and easily to produce different predetermined degrees of force over a wide range while having a comparatively restricted range of movement for any selected predetermined force.

An additional object is to provide an orthodontic headgear appliance including separate components that can be assembled readily and components of which can be selected to fit patients having heads of different size.

It is a particular object to provide a disconnectible connection between extraoral force-reaction gear and intraoral force-applying gear which is very precise and which will be disconnected immediately if a predetermined force which it is set to withstand is exceeded only slightly, and which gear components can be disconnected by a small amount of relative movement. Such disconnection will occur whenever the extraoral force-reaction gear is pulled excessively, whether intentionally or inadvertently, or is merely caught and the wearer exerts the force exceeding the predetermined force.

It is also an object to provide orthodontic gear having the foregoing capabilities which is light, compact, durable, of simple and economical construction and which can be fitted quickly, easily and accurately to the patient.

The foregoing objects can be accomplished by orthodontic gear including intraoral force-applying and extraoral force-reaction components connected by a component connector including a force-producing component which normally is yieldable relative to either the intraoral force-applying component or the extraoral force-reaction component but which has a restricted range of operating movement, and which can either be immobilized relative to the intraoral component or the extraoral component, or freed from the intraoral component or the extraoral component, such as by disconnection, so that the force-producing unit cannot snap back to produce sudden and violent relative contraction of the intraoral force-applying component and the extraoral force-reaction component.

BRIEF DESCRIPTION OF THE DRAWINGS

FIG. 5 is a side elevation of a representative component connector of headgear shown in FIGS. 1, 2 and 3, on an enlarged scale, and having parts broken away.

FIG. 6 is a longitudinal section through such component connector, shown connected to intraoral force-applying gear.

FIG. 7 is a longitudinal section through a portion of the component connector on a further enlarged scale.

FIGS. 8, 9 and 10 correspond respectively to FIGS. 5, 6 and 7, but show parts in a different relationship.

FIGS. 11 and 12 are longitudinal sections corresponding to FIGS. 6 and 7, respectively, and to FIGS. 9 and 10, respectively, but show parts of the component connector in another relationship.

FIG. 13 is a longitudinal section corresponding to FIGS. 7, 10 and 12 with the parts in still another relationship.

FIG. 14 is a longitudinal section corresponding to FIGS. 6, 9 and 11, but shows portions of the connector in still a different relationship.

FIG. 15 is a longitudinal section through the component connector shown in FIGS. 5 to 14, inclusive, with the various parts in exploded relationship.

FIGS. 16, 17, 18 and 19 are longitudinal sections through a portion of the component connector illustrated in FIGS. 5 to 15, inclusive, illustrating progressive stages in the assembly of the parts shown separated in FIG. 15.

FIG. 20 is a longitudinal section through a portion of a component connector corresponding to FIG. 19, but modified to provide a longer stroke of the parts, the construction of FIG. 19 being more suitable for utilization with a headcap such as shown in FIGS. 2 and 3, and the connector of FIG. 20 being more suitable for combination with a neckband such as shown in FIGS. 1 and 3.

FIG. 21 is a top perspective of a component connector of the same general type as shown in FIGS. 5 to 19, inclusive, but having a slightly modified construction.

FIG. 22 is a top perspective of the component connector shown in FIG. 21, with parts in exploded relationship.

FIG. 23 is a fragmentary top perspective of a component connector showing an alternative type of construction.

FIG. 24 is a top perspective corresponding to FIG. 23, showing another alternative type of construction.

FIG. 25 is a top perspective of a component connector with parts broken away, showing a modification of the construction of FIG. 21.

FIG. 26 is a top perspective of the component connector shown in FIG. 25, but having the parts in exploded relationship.

FIG. 27 is a fragmentary top perspective of the component connector of FIGS. 25 and 26, showing parts in a different relationship.

FIG. 28 is an enlarged top perspective of a fragment of the component connector shown in FIGS. 25, 26 and 27, showing details of construction.

FIG. 29 is a top perspective of the same structure as shown in FIG. 28, but with parts in a different relationship.

FIG. 30 is a longitudinal section through a fragment of a component connector corresponding to the connector fragment shown in FIG. 28, but of modified construction.

FIG. 31 is a longitudinal section through a fragment of a component connector corresponding to the fragment shown in FIG. 28 and FIG. 30, but illustrating a further modified type of construction.

FIG. 32 is a longitudinal section, FIGS. 33 and 34 are top perspectives, and FIG. 35 is a longitudinal section of different detailed modifications of portions of a component connector.

FIG. 36 and FIG. 37 are side elevations of a fragment of a component connector, showing parts in different relationships, and FIG. 38 is a top perspective of the same fragment of a component connector with parts in still a different relationship.

FIG. 39 is a side elevation, and FIGS. 40, 41, 42 and 43 are longitudinal sections through a portion of a component connector of another type, the several figures showing parts in different relationships.

FIG. 44 is a transverse section taken on line 44—44 of FIG. 41.

FIG. 45 is a top perspective of the same portion of the component connector showing the parts in exploded relationship.

FIG. 46 is a side elevation of a different type of component connector, certain features of which are similar to corresponding features of the component connector shown in FIGS. 25 and 26; FIG. 47 is a longitudinal section through such connector; and FIG. 48 is a transverse section taken on line 48—48 of FIG. 47.

FIG. 49 is an edge elevation of a modification of the type of component connector shown in FIGS. 46, 47 and 48.

FIG. 50 is a side elevation of a component connector abutting a different type of force-producing element, and having parts broken away.

FIG. 51 is a longitudinal section through such connector.

FIG. 52 is a side elevation of a component connector having still a different type of force-producing member, parts being broken away.

FIG. 53 is a plan of a preferred type of component connector with parts broken away, FIG. 54 is a top perspective of such a connector, and FIGS. 55, 56 and 57 are plans of such connector with parts broken away, such views showing parts of the connector in progressively different relationships.

FIG. 58 is an edge view of a component of the connectors shown in FIGS. 53 to 57, inclusive.

FIG. 59 is a top perspective of a component connector utilizing a helical compression spring as a force-producing member in combination with a disconnectible connection. FIGS. 60, 61 and 62 are longitudinal sections through the disconnectible connection showing parts in different relationships.

FIG. 63 is a top perspective of another type of component connector utilizing the combination of a compression spring and a disconnectible connection.

FIG. 64 is a top perspective of a component connector having a compression spring and a modified type of disconnectible connection.

FIG. 65 is a top perspective of a component connector having a disconnectible connection like that shown in FIG. 63 with a modified compression spring and connection arrangement.

FIG. 66 is a fragmentary top perspective of a portion of the component connector shown in FIG. 65 with parts in somewhat exploded relationship.

FIG. 67 is a top perspective of a component connector having a compression spring and connection arrangement similar to that shown in FIG. 65 in combination with a different type of disconnectible connection.

FIG. 68 is a top perspective of a further component connector having a compression spring, disconnectible connection and limit latch.

FIG. 69 is a longitudinal section through the component connector of FIG. 68.

DETAILED DESCRIPTION

Figure 1:
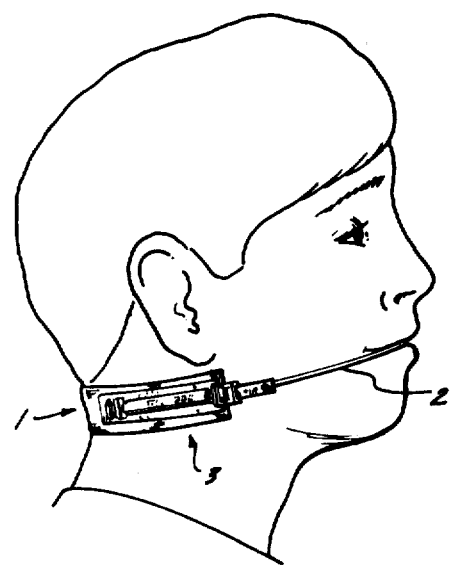
FIGS. 1, 2, 3 and 4 are side elevations of a patient shown wearing different types of orthodontic appliances to which the present invention pertains.
Figure 2:
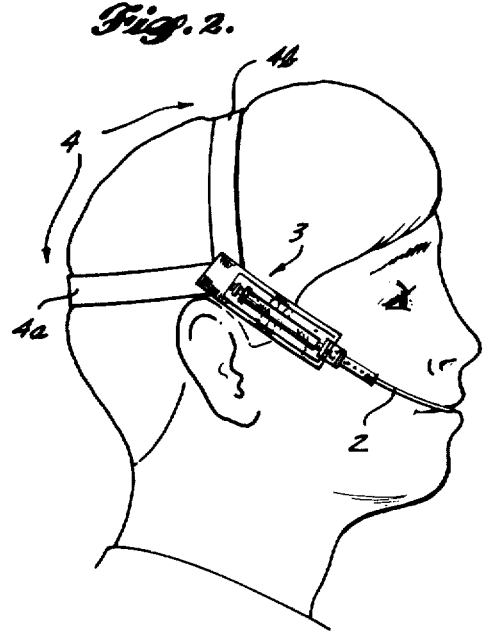
Figure 3:
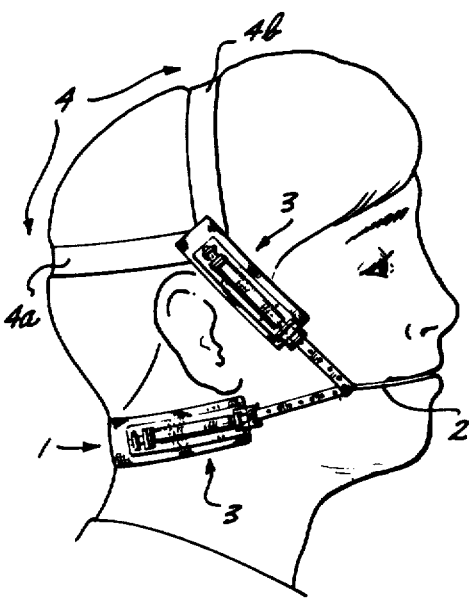

Orthodontic gear including an extraoral force-reaction component engageable with the wearer's head and/or neck and a force-applying component, such as an intraoral component, of various types has been used; representative types of gear are illustrated in FIGS. 1, 2 and 3. In each instance the gear includes two or three principal components, namely a force-applying component, by which a force is applied to a jaw, and an extraoral force-reaction band component, by which a reaction force is applied to the head and/or neck, and one or two component connectors which usually include a force-producing unit for producing a sustained force applied to the force-applying component. The term "intraoral" as used in the following description and claims is intended to include force-applying devices for orthodontic treatment which contact the exterior of the lower jaw, such as a chin cup.

In FIG. 1 the extraoral force-reaction component includes a neckband 1, a tie rod 2 connected to the intraoral component, and a force-producing connector unit 3. In FIG. 2 the extraoral force-reaction gear includes the headcap 4 composed of a lower band 4a extending around the back of the head and an upper band 4b extending across the top of the head. The ends of these bands are connected together and to the rearward end of the force-producing connector unit 3. In FIG. 3 the neckband 1 and the headcap 4 have individual force-producing connector units 3 which may be of the same type, and both of which are connected to the tie rod 2.

The force produced by the force-producing unit 3 in each instance applies a pull on the tie rod 2, which exerts a corresponding rearward force on the intraoral, or force-applying, component of the headgear to which the tie rod 2 is connected. It is evident that the pull produced by the neckband type of gear shown in FIG. 1 is downward and rearward from the mouth, whereas the pull produced on tie rod 2 by the headcap type of extraoral gear shown in FIG. 2 is upward and rearward from the mouth. By utilizing a combination of the neckstrap and the headcap as shown in FIG. 3, and arranging for the headcap force-producing connector unit and the neckband force-producing connector unit to produce predetermined forces of desired magnitude, the direction as well as the degree of pull exerted on the tie rod 2 can be selected over a considerable range.

Figure 4:
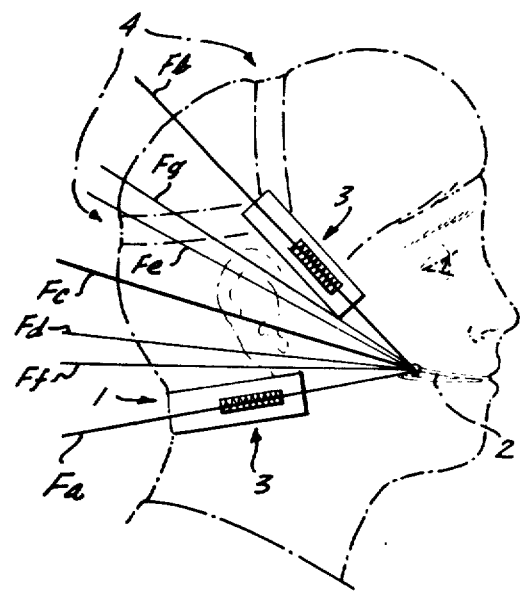

FIG. 4 illustrates diagrammatically various vectors representing different directions in which the pull on the tie rod 2 can be exerted by appropriately adjusting or setting the force-producing characteristics of the neckband and headcap force-producing units 3 and the lengths of connections between such force-producing units and the tie rod. If the headcap force-producing unit is adjusted to produce only a small force, the pull will be produced primarily by the neckband force-producing unit 3, so that the pull applied to the tie rod 2 will be primarily along the vector Fa. Alternatively, if the force-producing unit 3 of the neckband is adjusted to produce little or no force, the pull on the tie rod 2 will be exerted almost entirely by the headcap force-producing unit 3 and will act generally along the vector Fb. If the forces produced by the neckband force-producing unit 3 and the force produced by the headcap force-producing unit 3 are approximately equal, the resulting pull on the connector component 2 will be along a vector Fc approximately bisecting the angle between the force lines Fa and Fb extending through the neckband force-producing unit and the headcap force-producing unit, respectively.

By increasing the force produced by the neckband force-producing unit 3 somewhat and/or decreasing the force produced by the headcap force-producing unit 3 somewhat, the direction of pull on the tie rod 2 can be lowered, such as to the vector Fd. Alternatively, if the headcap force-producing unit 3 is arranged to provide an increased force and/or the neckband force-producing unit 3 is arranged to provide a reduced force, the direction of pull on tie rod 2 can be raised somewhat, such as to the line of vector Fe. If the force produced by the neckband force-producing unit 3 is increased to a greater extent and/or the force produced by the headcap force-producing unit 3 is reduced farther from equality, the vector of the pull on tie rod 2 can be lowered from the median vector Fc below the vector Fd, such as to the vector Ff. Alternatively, the headcap force-producing unit 3 can be arranged to produce a considerably greater force and/or the neckband force-producing unit 3 can be arranged to produce a considerably smaller force, so that the vector of the pull on tie rod 2 can be raised from the median vector Fc beyond the location of the vector Fe, such as to the location of the vector Fg.

In order to be able to arrange the pull on the tie rod 2 in different degrees and in different directions as discussed above, it is desirable for the force-producing units to be constructed for easy substitution in the gear or for easy adjustment to produce different degrees of force. Also it is important that the gear be designed so that snapback of the force-producing unit can be controlled reliably to avoid sudden or violent return contraction of the component applying the reaction force to the head or neck and the component through which the force is applied to the wearer's jaw. As an additional feature it is desirable to enable the various components of the headgear to be connected readily and disconnected at will or automatically in response to relative displacement of components more than a predetermined amount.

The principal features of the invention can be incorporated in a connector which connects an extraoral force-reaction band member, such as a neckband 1 or a headcap band structure 4a, 4b, with a tie rod 2, by which the pulling force is applied to intraoral force-applying gear. FIGS. 5 to 18 show one type of connector. Such connector includes a force-producing unit 3 having a backing 5 that can be attached suitably to the reaction force band component by being bonded or stapled to such component, as illustrated generally in FIGS. 1, 2, 3 and 4, and by the dot-dash line illustration of band means 4 in FIGS. 6, 9 and 14. Preferably the force-producing means carried by the backing 5 is enclosed in a housing tube 6. In the force-producing unit of FIGS. 5 to 19, the force-producing means is shown as a helical tension spring 7, slidable within the tube 6. The force-producing unit can be connected to the tie rod 2 by a side strap 8, having apertures 9 at regularly spaced intervals along its length for engagement by a hook on the end of the tie rod. The purpose of having a plurality of apertures in the strap is to enable the tie rod hook to be engaged in the appropriate aperture so that the proper length of connection between the force-producing unit and the tie rod for the particular patient can be selected.

Instead of the strap 8 being connected directly to the spring 7, it is preferred that an intermediate strap 10 be interposed between the strap 8 and the spring. The end of such intermediate strap adjacent to the spring is connected to a hook on the end of the spring by a connecting hook 11 preferably made of resilient strip metal or plastic. The shank of hook 11 is apertured to engage the spring end hook. The reversely-bent end of hook 11 passes through a slot in the end of the intermediate strap 10.

The hook 11 serves not only to connect the end of intermediate strap 10 to the adjacent end of spring 11, but such hook can serve the additional purpose of controlling snapback of the spring under certain conditions. During normal use of the appliance, as illustrated in FIG. 6, the intermediate strap extends beneath a bridge 12 upstanding from and integral with the backing 5 which preferably is of molded plastic material. As the strap 8 and intermediate strap 10 are pulled to the right relative to the backing 5 from the normal operating position shown in FIG. 6, the hook 11 will be pulled toward the bridge 12 until an upwardly bowed leaf part 13a of the return portion of the hook 11 is engaged with the bridge, as shown in FIG. 9.

The hook 11 is sufficiently flexible so that the upwardly bowed portion 13a can be depressed to enable that portion of the hook to be pulled beneath the bridge from the position of FIG. 9 to the position of FIG. 10. In order to contract the spring hook to this extent, it is necessary that the pull on the spring exceed the normal operating pull. The operating pull could, for example, be as much as thirty-two ounces and the pull required to slide the hook from the position of FIG. 9 to the position of FIG. 10 could be four or five pounds, for example. The amount of pull required would depend upon the relative heights of the bridge 12 and the hook 11 and the flexibility characteristics of the hook and of the bridge.

When the hook 11 has reached the condition of FIG. 10, very little additional pull is required to slide the upward bulge 13a of the hook to the right beyond the bridge to the position of FIGS. 11 and 12. When the hook has reached this position, if the pull on the strap 8 and intermediate strap 10 is relieved, the pulling force of spring 7 will be insufficient to pull the hook back under the bridge 12. Consequently, the hook 11 will constitute a limit latch which, in the latched position of FIGS. 11 and 12, will control the snapback of spring 7 by immobilizing the spring to prevent contraction movement of the spring from the position of FIG. 11, through the position of FIG. 10, to the position of FIG. 6.

The limit latch 12,13a will be engaged whenever the pull on tie rod 2 is sufficient to move the bow 13a of spring 11 under the bridge 12 to the position of FIG. 11. To effect such movement, the tie rod 2 must have been moved relative to the force-producing unit 3 and the head or neck engaging band means beyond a predetermined distance. In order to effect such relative movement between the tie rod and the force-producing unit and band means, it will be necessary to apply a separating force between the tie rod and the force-producing unit exceeding a predetermined value. Consequently the parts can be proportioned and spaced so that the limit latch will be latched automatically in response to predetermined relative displacement of the tie rod 2 and backing 5.

Moreover, the flexibility characteristics of the material of the hook 11, the width and thickness of the hook strip material, the hook proportions, and the height of the bow 13 with respect to the height of the bridge 12 can be selected so that the bow of the hook will be moved from the position of FIG. 9, through the position of FIG. 10, to the position of FIG. 11 automatically in response to exertion of a predetermined degree of separation force between the intermediate strap 10 and the backing 5. While the force exerted by spring 7 on the hook 11 in the position of FIG. 11 will be insufficient to move the hook back to the left under the bridge 12, the bow 13a can be depressed sufficiently by manual pressure applied to it so that the pull of spring 7, especially if aided somewhat by manual pushing, or in some instances manual pushing alone, will move the hook back under the bridge to the position of FIG. 10, whereupon the spring can return the hook to the position of FIGS. 6 and 7.

It is preferred that the backing 5 have a further bridge 14 at the side of bridge 12 remote from spring 7. Such bridge is lower than bridge 12 so that, while the hook 11 can pass under bridge 12, it cannot pass to the right, as seen in FIGS. 11, 12 and 13, beneath bridge 14. To insure a positive stop between the intermediate strap 10 and the bridge 14, the left end of such strap can be provided with abutments 15 projecting from the intermediate strap on opposite sides of hook 11 far enough to engage the left side of bridge 14 positively, as shown in FIG. 13.

During movement of the hook 11 from the position of FIG. 6 to the position of FIG. 9, the hook may tend to drag along the housing tube 6 and to drag a portion of spring 7 along such tube. To prevent appreciable lengthwise movement of the tube as a result of such dragging action, a stop projection 16 can be provided upstanding from the backing 5 for engagement by the tube end to limit its movement toward bridge 12.

While the limit latch 12,13a will immobilize the spring 7 in the condition of its maximum extension permitted by movement of the intermediate strap 10, the reaction force resisting band means 1 or 4 will still be connected to the tie rod 2 by the force-producing unit 3. A pulling force might be exerted on the intraoral component of the appliance sufficient to deform a portion of the appliance inadvertently by application of a strong force to it. Consequently, it is desirable for the tie rod 2 and the head or neck engaging force reaction band means, such as the neckband 1 or the headcap 4, to be disconnected automatically in response to application of a pulling force to the tie rod exceeding a value higher than the amount of pull required to latch the limit latch mechanism. The degree of pull to disconnect the tie rod might, for example, be seven pounds.

Disconnection between the tie rod 2 and the neckband or headcap preferably is accomplished by disconnecting the side strap 8 from the force-producing unit 3. Such a disconnectible connection is shown in FIGS. 5 to 22, inclusive, as including the widened end portion 17 of the intermediate strap 10 remote from the end of such strap carrying the abutments 15. Such widened end portion has a bridge 18, which can receive beneath it the side strap 8, as shown in FIGS. 8 to 12, inclusive. Spaced to the left of the bridge 18 and upstanding from the intermediate strap 10 is a stop rib 19 having a dual function. The left side of such rib is engageable with bridge 14 to limit movement of the intermediate strap to the left, and its opposite side is engageable by the adjacent end of the side strap 8 to limit its movement to the left relative to the intermediate strap 10.

The end portion of the side strap 8 remote from the tie rod 2 carries a return-bent load-releasing strip spring, preferably of metal. Such strip includes a return bend 20 hooked through an aperture in the form of a slit in the end portion of the strap 8 and a bowed spring leaf 21 projecting outwardly from the strap. The distance between the bridge 18 and the rib 19 is sufficiently great to accommodate the major portion of the length of the bowed leaf spring strip 21, so that such spring strip will fit between the bridge 18 and the rib 19, as shown in FIGS. 9, 10, 11 and 12, for example.

The flexibility of the bowed spring leaf 21 and the height of the bridge 18 are arranged so that the spring can be depressed to the condition shown in FIG. 13 by application of a pulling force to the tie rod 2 and side strap 8 of a predetermined value, such as the value of seven pounds mentioned above. When the bowed spring leaf has been depressed in this manner to slide beneath the bridge 18, the side strap 8 can be moved easily to the right from the position of FIG. 13 to the disconnected relationship of FIG. 14. Thus, while the intermediate strap 10 remains attached to the force-producing unit 3 by the limit latch hook 11 or the abutments 15 and the bridge 14, the side strap 8 and the intermediate strap 10 will be completely separated to disconnect the tie rod 2 from the head-engaging reaction force component such as the neckband 1 or the headcap 4.

FIGS. 5 to 14, inclusive, illustrate the parts of the force-producing unit 3 and representative intraoral gear in various relative positions. For purposes of illustration the intraoral gear is shown in FIGS. 6, 9, 11 and 14 as including the inner bow 2a of a double face bow, the tie rod 2 forming the outer bow. The inner tip 2b of the inner bow is reduced, as shown in FIG. 9, for insertion into the socket 2c of a molar band 2d, as shown in FIG. 6. If the face bow is grasped and pulled in the direction indicated by the arrow at the right of FIG. 9, the tip 2b of the face bow will be pulled out of the molar band socket 2c, while the inner bow of the face bow remains in the mouth.

It will be evident that the displacement of the face bow from the relationship to the force-producing unit 3 shown in FIG. 6 to the relationship shown in FIG. 9 is quite small, but is adequate to provide for maximum movement between the force-producing unit and the face bow which could be accomplished by tilting of the head. Alternatively, when the head is erect or untilted, the face bow can be moved relative to the force-producing unit to the position of FIG. 9 by grasping the face bow manually and pulling in the direction indicated by the arrow in FIG. 9. While such manual movement is undesirable, the degree of displacement of the face bow from the teeth indicated in FIG. 9 would be insufficient to withdraw the inner face bow from the mouth. If the face bow were released, the force exerted on the side strap 8 by the force of spring 7 acting on tie rod 2 would snap the double face bow inwardly farther in to the mouth, but the possible range of movement is quite small, i.e. the distance that stop rib 19 could move to bridge 14, as shown in FIG. 9. Consequently, if inner tips 2b strike soft tissue in the mouth, no substantial injury would occur.

Before the face bow could be displaced from the force-producing unit 3 sufficiently far to withdraw the inner bow 2a from the moutn, the limit latch bow spring 13a would have been moved through the position shown in FIG. 10 at least to the position of FIG. 11. By such displacement the limit latch bow spring 13a would have moved past the bridge 12, as illustrated in FIG. 11, to latched position. If the pull on the face bow were released at that time, the face bow would not snap back appreciably because the latch 12,13a would have immobilized the spring 7 in the condition shown in FIG. 11.

If the pulling force on the face bow were continued in the direction indicated by the arrow in FIG. 11, the tie rod 2 would be displaced further to pull the intermediate strap 10 from the position of FIGS. 11 and 12 to the position of FIG. 13, in which the abutments 15 and/or the latch bow spring 13a is engaged with the stop bridge 14. Continued pulling would cause the bridge 18 of the intermediate strap to exert a sufficient wedging action on the bowed leaf spring 21 to depress the bow for movement into the position beneath the bridge 18 shown in FIG. 13. Further continued pulling on the face bow would cause the spring 21 to slide out from under the bridge 18, so that the side strap 8 would be disconnected from the intermediate strap 10, as indicated in FIG. 14, and the face bow would be freely movable in the direction indicated by the arrow in FIG. 14 relative to the force-producing unit 3.

Representative values of force to effect latching of the limit latch 12,13a and to effect disconnection of the connection 18,21 have been stated. It is also important to design the appliance so that the tie rod 2 and the force-producing unit 3 are displaced through particular distances to effect latching of the limit latch and disconnection of the severable connection. It is desirable to enable the tie rod 2 and the force-producing unit 3 to be moved relatively to a greater extent when the force-producing unit is mounted on the neckband 1 than when the force-producing unit is mounted on a headcap 4 before the limit latch latches or the disconnectible connection is disconnected.

A typical example for the headcap-mounted force-producing unit 3 would enable the tie rod 2 and such force-producing unit to move through a distance within the range of five to eight millimeters before the limit latch bow 13 comes into contact with the bridge 12 in the position shown in FIGS. 9 and 10. This type of construction is illustrated in FIGS. 5 to 18, and particularly in FIG. 19. The parts of the appliance shown in FIG. 20 are the same as the parts of the appliance shown in FIG. 19, except that the length of the backing 5 between tube stop 16 and bridge 12 is somewhat greater than the distance between the stop and bridge in FIG. 19, and the length of the intermediate strap 10 between abutments 15 and stop rib 19 is correspondingly greater. The extent of normal movement permitted by the structure shown in FIG. 20 before the bow 13a engages the latch bridge 12 would be twelve to fourteen millimeters, for example, instead of five to eight millimeters as in the case of a headcap. The maximum yieldable extension and contraction relative movement of the strap 10 and force-producing unit should not exceed sixteen millimeters, or a force change of twelve ounces, during such movement. The construction shown in FIG. 20 is more suitable for association with a neckband 1 to accommodate excursions of the lower jaw and the head.

Relative movement of the tie rod 2 and the force-producing unit 3 after the latch bow 13a comes into engagement with the latch bridge 12 in order to secure the latch as shown in FIG. 12, would be the same whatever normal relative movement of the tie rod and force-producing unit could occur prior to such contact of the latch bow with the latch bridge. The additional extent of relative movement to secure the latch could be three millimeters, for example. In order to disconnect the side strap 8 and the intermediate strap 10 by relative movement of the bow spring 21 and the bridge 18 from the relationship shown in FIGS. 11 and 12 to the relationship in which the bow spring has just cleared the bridge 18 beyond the position of FIG. 13, could be an additional four millimeters or less.

Thus relative movement of the tie rod 2 and the force-producing unit 3 beyond the normal range of movement for a distance of three millimeters would effect latching of the limit latch to immobilize spring 7 whether or not a disconnectible connection is included. If the limit latch were omitted, such as by omitting the bridge 12, the disconnectible connection could be disconnected by a movement of four millimeters or less beyond the normal range of movement. If both the limit latch and the disconnectible connection are utilized, the latching of the limit latch and the disconnection of the connection would be accomplished by relative movement of the tie rod and the force-producing unit through a distance of approximately seven millimeters beyond the range of normal relative movement of the tie rod and the force-producing unit.

It is important for the limit latch to be operated, or for the side strap 8 to be disconnected from the force-producing unit 3, or both, before the intraoral component of the orthodontic gear, including the inner bow 2a and the tips 2b, has been withdrawn completely from the wearer's mouth, or ideally before the inner bow tips have been withdrawn from the molar band sockets, so that snapback of the face bow caused by the force-producing unit cannot occur when the inner bow of the double face bow is in a position such that snapping-back action of such bow might cause the inner bow tips 2b to penetrate an external portion of the face. Consequently, the normal range of relative movement of the side strap 8 and the force-producing unit 3 must be sufficiently small so as to initiate latching action of the limit latch to immobilize the spring 7, and/or to effect disconnection of the side strap 8 from the force-producing unit 3, before the inner bow 2a and tips 2b have been withdrawn completely from the mouth of the wearer, such as when the inner bow has not been pulled appreciably farther outward from the mouth than the position of the inner bow shown in FIG. 11.

Both to latch the limit latch and to disconnect the side strap 8 from the intermediate strap 10, will of course, require a greater displacement of the intraoral device from the force-producing unit 3 beyond the normal range of movement of these parts. Where a limit latch and a disconnectible connection are arranged in series, therefore, the range of movement of the intraoral device relative to the force-producing unit should be as small as reasonably possible, while still affording sufficient relative movement between the side strap 8 and the force-producing unit 3 to enable the hook of the tie rod 2 to be engaged in the appropriate hole 9 of the side strap 8 and to accommodate reasonable excursive motion of the lower jaw relative to the head without effecting latching of the limit latch or disconnection between the side strap 8 and the force-producing unit 3.

The strap 10 is shown in FIGS. 5, 6 and 7 in approximately the middle of its operating range. If pull on the side strap 8 were completely relaxed, the force produced by spring 7 would pull the intermediate strap 10 to the left, as seen in FIGS. 5, 6 and 7, until the stop rib 19 is drawn into abutment with the right side of the low bridge 14. The other extreme of the normal range of relative movement of the tie rod 2 and force-producing unit 3 is reached when the bow spring portion 13a of the hook 11 is engaged with and starts to be drawn under the bridge 12 of the limit latch mechanism.

With the parts of the orthodontic appliance in the normal treating relationship of FIGS. 5, 6 and 7, the spring 7 of the force-producing unit would exert a sustained and substantially uniform force on the face bow 2,2a directed inwardly of the mouth. As explained in connection with FIGS. 1 to 4, inclusive, it may be desirable to alter the force applied to the face bow for treating different orthodontic conditions. While the spring 7 could be preliminarily stressed to produce substantially a predetermined force for application to the intraoral device, so that the force produced could be altered by selecting different preliminary stressed springs, the force-producing unit 3 shown in the appliance of FIGS. 5 to 22 can be adjusted so as to produce different degrees of force.

To provide for selective adjustment of the spring 7 by increments over a considerable range of selectible average treatment forces, the end of spring 7 remote from the hook 11 is attached to one end of an anchor strap 22. This anchor strap carried buttress teeth 23 spaced along its length distances corresponding to increments of force, for which force increments the stress of and force produced by spring 7 can be altered without changing appreciably the variation in force which occurs as a result of relative movement of the tie rod 2 and the force-producing unit 3 during normal use of the gear. The abrupt sides of such teeth face the spring so that they an engage an edge of a bridge 24 remote from the spring formed by a band having its length extending transversely of the anchor strap 22, beneath which bridge the anchor strap can extend. The end portion of anchor strap 22 remote from spring 7 can be confined by tucking it through a keeper slot 25 in the backing 5 at the side of the anchor bridge 24 remote from the spring 7.

The buttress-toothed anchor strap 22 and the bridge 24 upstanding from the backing 5 constitute a linear ratchet which can be adjusted to alter the force produced by the spring 7. The end of the anchor strap remote from that spring is simply threaded beneath the bridge 24 and pulled so that successive teeth 23 engage the bridge until the spring 7 has been stressed to the extent necessary for the spring to produce the desired degree of orthodontic treatment force which is appied to the intraoral component of the appliance. The free end of the anchor strap is then tucked through the slot 25 of the backing 5.

The various parts of the force-producing unit 3 are shown in exploded relationship in FIGS. 15 to 22. The procedure by which such parts can be assembled into the force-producing unit shown in FIGS. 5 to 14 is illustrated in FIGS. 16, 17 and 18. The end of intermediate strap 10 remote from its bridge 18 is threaded first beneath bridge 14 and then beneath bridge 12 carried by the backing 5. The spring-connecting hook 11 can then be inserted through the slot in the end of the intermediate strap, as indicated in broken lines in FIG. 16, and one hook of the spring 7 can be threaded through the aperture of hook 11.

Next the aperture of the anchor strap 22 can be engaged with the hook on the other end of the spring, and the housing tube 6 can then be slipped lengthwise over the anchor strap and the spring into the position shown in FIG. 17. Next the free end of the anchor strap 22 can be threaded beneath the anchor bridge 24 and pulled to the left until the selected tooth 23 of the linear ratched corresponding to the desired force to be produced by spring 7 has engaged the left side of the anchor bridge.

The tail of the anchor strap can then be tucked through the keeper slot 25 as shown in FIG. 18.

Finally, the end of the side strap 8 remote from the load-releasing spring 20 is threaded beneath the bridge 18 of the intermediate strap 10 in the direction indicated by the arrow in FIG. 18. When the left end of such side strap has been seated between the bridge 18 and the stop rib 19, as shown in FIG. 6 for example, the hook on the end of the tie rod 2 can be engaged in an aperture 9 of such side strap, selected to provide the proper spacing between the neckband 1 or headcap 4 and the intraoral component of the appliance, to enable the force produced by the force-producing unit to be applied in the desired manner to the intraoral component. Any tag end of the side strap extending forwardly beyond the aperture 9 in which the hook of the tie rod 2 is engaged can then be cut off, if desired.

In providing a movement-limiting means, such as a limit latch, and/or a disconnectible connection for the side strap of an orthodontic appliance, consideration should be given to the amount of movement that should be afforded for the side strap before the movement-limiting means, such as a limit latch is actuated or the disconnectible connection is disconnected, which considerations have been discussed above. Because of excursions of the head and upper jaw relative to the neck, excursions of the lower jaw relative to the head and excursions of the lower jaw relative to the neck, more lengthwise movement of the side strap 8 should be permitted before the latch is latched or the connection is disconnected if the force-producing unit is used in conjunction with a neckband 1 than would be required where the force-producing unit is used in connection with a headcap 4. A comparison of the structures shown in FIGS. 19 and 20 indicates the alteration in design which will provide a greater range of normal movement between the side strap 8 and the force-producing unit 3 for a neckband installation than for a headcap installation.

As has been discussed above, contraction movement of the spring 7 to the left is limited by engagement of the stop rib 19 on the intermediate strap 10 with the right side of the low bridge 14. In FIGS. 19 and 20 the stop rib 19 is the same distance from the low bridge 14, indicating the normal pull is being applied by the spring 7 through the side strap 8 to the tie rod 2. Movement of the intermediate strap 10 to the right, both in the construction of FIG. 19 and in the construction of FIG. 20, is limited by engagement of the limit latch bow spring 13a with the left side of the bridge 12.

The structure of FIG. 19 is intended for use with a headcap 14, and the structure of FIG. 20 is intended for use with a neckband 1, because in FIG. 19 the bridge 12 is closer to the tube stop 16 than it is in FIG. 20. Consequently, the latch bow spring 13a can move farther to the right from the position shown when the structure of FIG. 20 is used than where the structure of FIG. 19 is used. The extent of the normal range of movement of the side strap 8 relative to the force-producing unit 3 can be altered simply by changing the length of the interval between abutments 15 and stop rib 19 of the strap 10 and locating bridge 12 farther from or closer to the tube stop 16 to alter the position of the adjacent end of spring 7 at opposite ends of the normal range of movement of the side strap 8.

While FIG. 9 shows the abutments 15 as passing beneath the crossbar of the bridge 12, the central portion of the bridge can be stiffened to reduce its deflection and notches can be provided beneath the opposite ends of the bridge crossbar to permit passage of the abutments 15, as shown in the bridge 12' of FIGS. 21 and 22. The bow spring 13a of the limit latch would engage the thickened central portion of the bridge crossbar and be depressed, whereas the abutments 15 spaced transversely of the intermediate strap 10, as shown best in FIG. 22, would pass through the downwardly opening notches in the opposite end portions of the bridge crossbar but engage bridge 14 to provide a positive stop. With the exception of this modification, the appliance shown in FIGS. 21 and 22 is similar to that of FIGS. 5 to 20, inclusive.

FIG. 23 shows an alternative type of keeper arrangement for the tail of the spring anchor strap 22. In this instance the anchor strap is held in position by an upright anchor pin 26 upstanding from the backing 5 and substantially straight throughout its length. Such pin is engaged in an aperture 23' selected from one of a row of apertures arranged along the length of the spring anchor strap corresponding to different selected force-producing stresses of the spring 7. The anchor pin can lean to some extent toward or away from the spring 7, as may be preferred for most convenient engagement of an aperture in the strap with the pin.

At the side of the anchor pin 26 remote from spring 7, arranged in series relationship, are two or more cantilever bridges 24' mounted alternately at opposite sides of the strap. At the side of the strap opposite the root of each cantilever bridge is a wedge-shaped side stop 27 spaced transversely of the backing 5 to some extent from the tip of the cantilever bridge. The tip of each bridge has an under bevel on a skew angle, inclined toward the spring and the root of the bridge. Such combination of side stops and cantilever bridges enables the tail of the anchor strap beyond the anchor pin to be swung to and fro, first toward the stop 27 nearest the anchor pin 26, next in the opposite direction while being slid up the inclined side of such stop and down under the cooperating cantilever bridge 24', and then in the opposite direction to be slid up the inclined side of the next farther removed stop 27 and downward to be caught under the cantilever bridge 24' cooperating with that stop.

While any number of cooperating stops and cantilever bridges could be arranged in series lengthwise of the anchor strip, two such successive stops and cantilever bridges constitute a satisfactory keeper for the tail of the anchor strap. The adjacent end of the housing tube 6 for the spring 7 can be maintained in position centered relative to the keeper structure by posts 28 upstanding from the backing 5 and spaced transversely of the tube to receive its end between them as shown in FIG. 23. A particular advantage of this type of construction is that the tail of the anchor strap can be secured in any selected position of adjustment simply by manipulation with the fingers. By holding the tail of the anchor strap in the proper longitudinally adjusted position as it is slid up the ramp of the first stop 27 and tucked under the first cantilever bridge 24', the desired aperture 23' can be pressed down over the anchor pin 26. The portion of the anchor strap tail beyond the first keeper element can then be swung farther in the same direction and back to be engaged with the next keeper element.

In the modified keeper construction shown in FIG. 24, a single keeper element including the combination of a stop 27 and a cantilever bridge 24' is combined with a keeper slot 25 through which the end portion of the anchor strap tail is tucked after the tail has been initially caught under the cantilever bridge 24' of the first keeper element. In this modification the end of the housing tube 6 is shown as being held down more positively by a band 29 bridging the end of the tube instead of lateral movement of the tube end being restrained simply by being lodged between posts 28 as shown in FIG. 23.

In the force-producing unit 3 shown in FIGS. 25 and 26, the central portion of the spring housing tube 6 is confined by a wider band 29' located generally centrally of the backing 5. Such band will deter buckling of the tube by the force of a stressed spring 7 even if the material of the tube is quite flexible. Also in this modification only a single keeper element including a stop 27 and a cooperating cantilever keeper bridge 24'' is shown. Such cantilever bridge, however, is longer than the bridges 24' shown in FIGS. 23 and 24, so as to confine the tail of the anchor strap more reliably than would a single keeper element of the type shown in FIG. 23.

The connection of the side strap 8 to the force-producing unit 3 shown in FIGS. 25 to 29, inclusive, like that described in connection with FIGS. 5 to 22, has both a limit latch and a disconnectible connection. The disconnectible connection including the bowed spring leaf 21 cooperating with the bridge 18 is the same as that described in connection with the apparatus of FIGS. 5 to 22. FIG. 27 shows how the side strap 8 can be assembled with the intermediate strap 10, as also illustrated in FIG. 18.

The limit latch structure shown in FIGS. 25 to 29 differs from the limit latch structure of FIGS. 5 to 22 in that a molded buttress tooth 13b is substituted for the bow spring 13a of the limit latch of FIGS. 5 to 22. Preferably the backing 5 and the intermediate strap 10 of FIGS. 25 and 26 are molded of plastic material. An inclined or sloping side of the buttress wedging member 13b will engage with the left side of the latch bridge 12''. Bridge 12'' also serves as a stop for the end of tube 6 as the side strap 8 is pulled in the direction indicated by the arrow in FIG. 25. Such buttress tooth 13b and/or the bridge 12'' will be sufficiently yieldable to enable the buttress tooth to be pulled beneath the bridge when a force of predetermined maximum value is applied to the side strap 8 and to the force-producing unit 3 tending to separate them.

When the buttress tooth 13b has been pulled beneath the bridge 12'' to the side opposite that shown in FIG. 25, the force of the spring 7 will be insufficient to pull the abrupt or sheer side of such tooth back under the bridge. The shoulder 15' of the enlarged end of the inermediate strap 10, with which enlarged end the spring is engaged, will abut the left side of the bridge 12'' after the buttress tooth 13b has passed to the right of such bridge to prevent the intermediate strap 10 and the spring 7 from being extended relative to the backing 5 to a greater extent. The buttress tooth 13b can be moved manually at will back under the bridge 12'' from the latched position shown in FIG. 28 by swinging the intermediate strap 10 relative to the bridge as shown in FIG. 29. The corners of the buttress tooth 13b are clipped to provide wedging chamfers that can be pushed against the right side of the bridge to wedge it up sufficiently to enable the buttress tooth to move back beneath the bridge to the position of FIG. 25.

In FIG. 30 a further modification of the limit latch is shown. In this instance a bow spring 13c is formed as an integral part of the intermediate strap 10. As in the types of limit latches described previously, a sufficient pull on the intermediate strap to the right, as seen in FIG. 30, will effect a wedging action between the bridge 12'' and the bow spring 13c so that one or both of them will yield sufficiently to enable the bow spring to pass to the right beneath the bridge 12'' into latched position. Abutment of the shoulder 15' of the strap end with the left side of the bridge will limit extension movement of the intermediate strap and the force-producing unit. To release the limit latch, the bow 13c can be pressed downward manually and pushed to the left so that, with the aid of the spring 7, the bow can be moved back beneath the bridge 12'' to the position shown in FIG. 30.

The parts are shown in FIG. 30 at the right end of the normal operating range. The left end of the operating range is established by engagement of the stop rib 19 with the right side of the bridge 12''. Despite the ability of the stop rib 19 to effect such stop action, the intermediate strap 10 can be inserted beneath the bridge 12'' from left to right as seen in FIG. 30 during initial assembly of the parts by effecting such insertion before the housing tube 6 is inserted over the spring 7, because, as will be seen in FIG. 30, the intermediate strap 10 is raised by such tube to the extent of its thickness.

In FIG. 31 another modification of the limit latch is shown in which a metal strip 11', forming a bow spring 13d having a configuration different from the hook 11 shown in FIGS. 5 to 22, has an end portion extending through transverse slots in an intermediate strap 10 generally of the type shown in FIGS. 25 and 26.

A free end portion of the strip 11' can be depressed downward into a slot 11'' extending lengthwise of the intermediate strap 10 to facilitate passage of the bow spring 13d beneath the bridge 12'' when strap 10 is moved to the right as seen in FIG. 31. Movement of the intermediate strip 10 to the right will be limited by abutment of the shoulder 15' with the left side of the bridge, and return movement of the intermediate strap from latched position of the latch will be prevented by the left side of the spring bow 13d engaging the right side of the bridge 12''. The latch can be released by pushing the spring bow 13d back to the left of the crossbar of the bridge, which will also press the free end of the strip 11' downward into the slot 11'' of the intermediate strap 10, so that such bow can pass beneath the bridge crossbar. Again, the normal operating range of movement of the intermediate strap 10 relative to the force-producing unit 3 will be established between the position shown in FIG. 31 and the position to the left at which the stop rib 19 is engaged with the right side of bridge 12''.

Where the force exerted by the spring 7 in the various force-producing units described above can be altered to provide the desired treatment, it is preferred that there be calibration means to indicate the degree of force which is being produced by the spring in its different adjusted conditions. Such calibration means are shown in FIGS. 5, 8 and 21 to 27, as including a calibration scale 30 graduated in ounces, having lines corresponding to such graduations that are visible through the transparent housing tube 6 for coordination with the end of the spring 7 remote from the side strap 8. Thus in FIGS. 5 and 8 the spring 7 is set to provide an average working pull of sixteen ounces. In FIG. 21 the spring is set to provide an average working pull of eight ounces. In FIGS. 23 and 24 the spring is set to provide an average working pull of thirty-two ounces.

Reference is made to the "average" working pull because considerable movement of the side strap 8 relative to the force-producing unit 3 occurs in the neckband type of appliance shown in FIG. 1 and the pull at one end of the working range will be different from the pull at the opposite end of the working range. Some range of movement is required to hook the tie rod 2 to the side strap 8. After such attachment, when the head and lower jaw are held in the most usual position the right end of the spring 7 should be aligned with the zero index mark 31, as shown in FIG. 5. When the right end of the spring is aligned with such index mark, the pull produced by the spring will be that designated by the calibration line 30 aligned with the left end of the spring. When the spring moves to the left of the zero index mark 31 the pull of the spring will be somewhat reduced, as indicated by the minus signs at the index 31. When the right end of the spring is pulled to the right beyond the zero index mark, as indicated by the plus signs in FIG. 8, for example, the pull produced by the spring will be greater than the line of the calibrations 30 with which the left end of the spring is in registration.

In any case the bridge 14, abutments 15 and stop rib 19 limit relative movement of the intermediate strap 10 and the force-producing unit 3 in the normal range of resilient movement to a distance less than the extent to which the spring anchor strap and the left end of the spring can be moved to alter the amount of average force produced by the spring. The operating range of the right end of the spring is usually from six to twelve millimeters and never over sixteen millimeters, whereas the left end of the spring should be adjustable over a range of twelve to forty millimeters to provide a desirable range of predetermined forces to be applied to the tie rod 2.

In FIG. 32 a limit latch is combined directly with the side strap 8 instead of an intermediate strap 10, and no disconnectible connection is provided. The left end of the side strap 8 overlaps the right end of the backing 5, and an enlargement 15" is provided on the left end of the side strap to which the right end of the spring 7 is connected directly. A stop rib 19' is provided on the backing 5, which is engageable by the left end of the side strap 8 to limit relative contracting movement of the side strap and the backing 5 at the minimum pull end of the normal stroke. The maximum pull end of the normal stroke is reached when the limit latch buttress tooth 13e comes into engagement with the left side of the bridge 12, as discussed in connection with the operation of the limit latch tooth 13b and the bridge 12" in the description of the appliance shown in FIGS. 25, 26 and 28.

In the form of the device shown in FIG. 32 a predetermined excessive pull applied to the tie rod 2 will move the buttress tooth 13e beneath the bridge 12 to its right side, as shown. A ramp on enlargement 15" constituting a stop member will be engaged with the left side of the bridge 12 to prevent further extension movement of the side strap 8 and the backing 5. The spring 7 will be immobilized when the parts have reached this condition. The buttress tooth 13e has clipped corners like the corners of the tooth 13b shown in FIGS. 28 and 29. Consequently, when it is desired to release the limit latch, the side strap 8 can be swung relative to the backing in the manner indicated in FIG. 29, so that the buttress tooth can move back to the left beneath the bridge 12. Initial assembly of the side strap 8 and the backing 5 can be accomplished simply by threading the right end of the side strap beneath the bridge 12 from left to right.

FIGS. 33, 34 and 35 show linear ratchet arrangements which can be used to connect different components of the gear where it is desired to be able to establish different lengths of straps for different patients. In FIG. 33 such a linear ratchet arrangement is shown as being used to connect the side strap 8 and an intermediate strap 10 of the type shown in FIGS. 25 and 26, while at the same time providing a connection disconnectible automatically in response to the occurrence of a predetermined excessive degree of pull. The linear ratchet includes buttress teeth 32 molded integrally with the side strap 8. These buttress teeth are of a height to snap successively beneath the bridge 18 as the strap is pulled to the left relative to the intermediate strap 10 in the direction indicated by the arrow.

When the desired length of strap 8 has been reached with an abrupt side of a buttress tooth 32 engaging the left side of bridge 18, the end of side strap 8 projecting to the left of the bridge 18 may be cut off appropriately so that the cut end will abut the stop rib 19 and leave only a single buttress tooth or member at the left of the bridge. When the pull on the side strap 8 exceeds a predetermined value, the buttress tooth engaging the left side of the bridge 18 will wedge the bridge outward and be pulled beneath the bridge to disconnect the connection between the intraoral component and the force-producing unit in the manner described above.

In FIG. 34 the linear ratchet construction is shown as being used to connect a tail strap or tongue 33 provided on the end of backing 5 remote from the side strap to an extraoral component reaction band member such as the headcap 4. A stop rib 34 is provided on such headcap so that, when the tail strap has been threaded beneath a latch bridge 35 for a distance sufficient to provide the desired fit, the end of the tail strap projecting beyond such bridge can be cut off appropriately to fit between the bridge and the stop rib and to leave only a single buttress tooth or member at the left of the bridge. Excessive pull beyond a predetermined value will cause the abrupt side of such member to wedge the bridge outward and disconnect the connection afforded by the linear ratchet tooth or buttress member 32 engaging the left side of latch bridge 35.

Instead of providing the stop rib 19 as shown in FIG. 33, or the stop rib 34 as shown in FIG. 34, a suitable stop can be formed by providing a second bridge 34' spaced to the left of bridge 18, as shown in FIG. 35. If this construction is used for tail strap 33, the second bridge 34' would replace the stop rib 34. With such a construction it would be desirable for the bridge 34' to be made somewhat higher than the bridge 18, so that the strap 8 could be pulled to the left to a desired position of adjustment more easily than it could be pulled to the right to move a ratchet tooth under bridge 18. Again, when the desired adjusted relationship between strap 8 and the bridge has been established, the left end of the linear ratchet strap can be cut off so that disconnection of the linear ratchet strap and the member carrying the bridge can be accomplished by passage of a single buttress tooth beneath the bridge.

In FIGS. 36, 37 and 38 an alternative type of disconnectible connection between the backing 5 and a head-engageable reaction component, such as the headcap 4, is shown. By such connection headgear components of different size can be connected readily to the force-producing unit 3. In this instance the backing member has a short tail strap 33' or tongue insertible beneath the bridge 35 when moved in the direction indicated by the arrow in FIG. 38. The backing 5 carries a bowed leaf spring 36, preferably of strip metal, which can be depressed either directly manually, or by wedging action by pushing the left end portion of such spring against the right side of bridge 35 as seen in FIGS. 36 and 38. Such bowed leaf spring will snap up at the left side of bridge 35 when the left end of the tail strap 33' has reached a position adjacent to the stop rib 34, as shown in FIG. 36. If an excessive pull is exerted between the force-producing unit 3 and the headcap 4, the connection between the tail strap 33' and the headcap will be disconnected as shown in FIG. 37 by yielding of the spring 36 in the manner described in connection with spring 21, as shown in FIGS. 13 and 14.

In the type of appliance shown in FIGS. 39 to 45, inclusive, the adjacent end portions of the side strap 8 and the intermediate strap 10' overlap between parallel walls 37, connected by a bridge 38. The lower portions of such walls have barbed projections 39 insertable through slots 40 in the end portion of the backing 5 adjacent to the tie rod 2. The walls 37 will have sufficient resilience to enable their lower edges to be moved toward each other so that the side barbs of the projections 39 will snap beneath the backing 5 to hold the barbs securely in engagement with the underside of the backing 5.

The end of the housing tube 6 adjacent to the walls 37 has a top bevel, and a notch 41 in its lower side is engageable with a block 42 projecting upward from the backing 5 to prevent rotation of the tube relative to the backing. The end of intermediate strap 10' has a cross-rib 43 integral with it and the cross-rib side 44 facing the spring 7 is steeply inclined. Such rib side is engageable with the complementally inclined side 45 of cross-rib 46 on the adjacent end of the side strap 8.

A hook on the end of spring 7 is engaged in a hole in the adjacent end of intermediate strap 10', so that the spring tends to pull the strap to the left as seen in FIGS. 40 to 43. In the absence of any opposing force the intermediate strap will be pulled into the position of FIG. 40 and held in that position by engagement of the inclined side 44 of the cross-rib 43 with the right edge of a crossbar 47 connecting the two upright walls 37. With the intermediate strap in this position, the end of side strap 8 remote from the cross-rib 46 can be threaded between the walls 37, beneath the bridge 38 and above the cross-rib 43 of the intermediate strap 10' in the manner illustrated in FIG. 40.

As the cross-rib 46 of the side strap 8 moves between the walls 37, the inclined side 45 of the downwardly projecting cross-rib 46 will engage the upper portion of the inclined side 44 of the cross-rib 43 on intermediate strap 10'. As the side strap 8 is pulled to the right, the engagement of its cross-rib side 45 with the cross-rib side 44 of intermediate strap 10 ∝ 0 will pull the intermediate strap to the right in opposition to the force exerted by spring 7 as indicated in FIG. 41. The pressure between the inclined sides 45 and 44 will tend to wedge the end of side strap 8 carrying cross-rib 46 upward. Engagement of the upper side of such strap with the bridge 38 will limit such upward movement.

A top lug 48 projects upward from the upper side of the side strap 8 adjacent to the cross-rib end of such side strap, which lug is engageable with the right edge of the bridge 38 when the side strap and the intermediate strap 10' have been pulled to the position of FIG. 42. The wedging action produced by the engagement of the steeply inclined side 44 of cross-rib 43 and the steeply inclined side 45 of cross-rib 46 will snap the end of the side strap upward to the position of FIG. 42, so that the lug will engage the edge of the bridge if the pulling force on the tie rod 2 to the right is relieved. Such engagement of the stop lug with the bridge edge will immobilize the spring 7 so that the cross-rib sides 44 and 45, the stop lug 48 and the bridge 38 constitute a limit latch operating in the manner described above for limit latches of other forms of the present invention.

If the pulling force exerted on the tie rod 2 increases appreciably beyond that required to pull the side strap 8 and the intermediate strap 10' to the positions shown in FIG. 42, the straps will be moved into the positions shown in FIG. 43 in which the end portion of the side strap 8 clears the bridge 38, whereupon the wedging force between the steeply inclined cross-rib sides 44 and 45 will cause the end of the side strap 8 to be slid upward to the broken-line position shown in FIG. 43. In such position the side strap will be free from the intermediate strap to effect disconnection of the disconnectible joint. When the cross-rib 43 is thus freed from the pulling force on the side strap 8, the stress of sprig 7 will snap the intermediate strap back to the left from the position of FIG. 43, so that the cross-rib 43 will engage the stop bar 47, as shown in FIG. 40, but such snapback movement of the intermediate strap will cause no difficulty because the intermediate strap is substantially completely enclosed within the housing formed by the backing 5, the sides 37 and the bridge 38.

In order to insure that the steeply inclined faces 44 and 45 of the cross-ribs 43 and 36 are retained reliably in engagement until the left end of the side strap 8 has been drawn beyond the right edge of bridge 38, it is desirable to provide rails 49 inclined from their ends adjacent to spring 7 outwardly away from the backing 5, which rails are integral with such backing. The ends of such rails can be connected by an end wall 50 which projects from the backing 5 beyond the edges of the rails to form a stop flange engageable by the end of intermediate strap 10' when it has reached its limiting position to the right as seen in FIG. 43.

The parts of the appliance shown in FIG. 45 can be assembled by first mounting the element including walls 37 and bridge 38 on the backing 5 by pushing the barbed projections 39 through the slots 40. The intermediate strap 10' can then be moved into the chamber between the walls 37 lengthwise from right to left, as seen in FIGS. 40 to 43, inclusive. Next the hook of spring 7 can be engaged with the spring-anchoring aperture of the intermediate strap, and the housing tube 6 can be slid over the spring until its notch 41 is engaged with the block 42. Finally the side strap 8 can be threaded between the walls 37 and beneath bridge 38 from left to right, as stated above and shown in FIG. 40.

The spring 7 of the appliance shown in FIGS. 39 to 45 can be of the preliminarily stressed type, or the initial stress of the spring can be adjustable by the arrangement shown in FIG. 39. The anchor strap 22 connected to the left end of the spring 7 can be secured to the backing 5 by a headed pin 51 extending through an aperture 23' in the spring anchor strap 22 and through the backing 5. To maintain the tube 6 in proper lengthwise position, the left end of such tube may have a tab integral with it interposed between the anchor strap and the backing, which is also apertured for penetration by the securing pin 51.

The degree to which the spring 7 is stressed, and consequently the magnitude of the pull exerted by the spring on the tie rod 2, can be altered by shifting the spring anchor strap 22 lengthwise to engage the headed pin 51 in different apertures 23' in the spring anchor strap. The farther to the left such strap projects, the greater will be the stress of the spring 7, and correspondingly greater will be the pull exerted on the tie rod 2. The magnitude of the spring stress can be indicated by calibrations 30 with which the end of the anchor strap 22 can be aligned. As discussed in connection with FIG. 5, for example, the calibrations can be in increments of eight ounces, and the calibrations can be located to cooperate with the end of the anchor strap 22 to indicate the stress of the spring.

Alternatively, the calibrations can be placed on the anchor strap itself opposite the respective apertures, as shown in FIG. 39 and designated 30'. While the calibrations on the right side of the spring anchor strap signify ounces of average pull on the tie rod 2, such spring anchor strap can be used with various springs having different load characteristics. All helical tension springs, however, have a deflection rate cooresponding substantially linearly to the pull exerted by such a spring. Especially if the anchor strap 22 is to be used in association with springs having different characteristics, the spring load adjustment apertures can simply be numbered 1, 2, 3, 4 and 5, as indicated along the left margin of the spring anchor strap in FIG. 39.

The calibrations at the left of FIG. 39 are stated to indicate average values of pull on the tie rod 2. The calibrations are arranged to designate the exact value of the pull on such tie rod when the stop lug 48 on the side strap 8 is in registration with the zero index mark 31' on the bridge 38. When such stop lug is at the left of the zero index mark, the pull exerted on the tie rod will be somewhat less than the value indicated by a calibration 30 or 30'. Conversely, when the stop lug is at the right of the zero index mark 31', the pull on the tie rod will be somewhat greater than that indicated by a calibration 30 or 30'.

The force-producing unit 3, shown in FIGS. 46, 47 and 48, is similar to that shown and described in connection with FIGS. 25 and 26. In this instance, however, the side strap 8' carries the member 13b of the limit latch and is connected directly to spring 7. The opposite end of strap 8' is connected to the tie rod 2e by a swivel connector 52. In this instance the tie rod is in the form of a J-hook. The shank of such J-hook extends under bridges 53 arranged in series on the backing 5. Such backing is secured to a neckband 1, and an auxiliary headband 4c is attached directly to the backing to extend upward across the head just forward of the ear to deter sagging of the side portion of the neckband.

FIG. 49 also shows a force-producing unit 3 similar to that shown and described in connection with FIGS. 25 and 26, but in this instance the housing tube 6' is made of comparatively rigid transparent plastic material of preformed shape, so that it will maintain its shape without provision of the tube-retaining band 29' shown in FIGS. 25 and 26 despite the spring 7 housed within it being preliminarily stressed or being stressed to a considerable degree by lengthwise extension of anchor strap 22.

The force-producing unit 3' shown in FIGS. 50 and 51 utilizes a helical compression spring for producing the force applied to the intraoral component of the appliance instead of a helical tension spring as used in the appliances shown in FIGS. 5 to 49, inclusive. In this unit the compression spring 7' is received in housing tube 6', and its right end is seated on an internal flange at the right end of such tube. The side strap 8 has an extension 8" connected to a plunger rod 54 extending axially through the spring and carrying a plunger head 55 engageable with the left end of spring 7'.

The backing 5' has a row of holes 56 extending lengthwise of it, which holes are spaced apart correspondingly to increments by which the compression spring 7' could be contracted to alter the force which it produces and which is applied to the side strap 8. The housing tube 6' has a tab projecting from its left end remote from its internally flanged end on which the spring 7' seats. This tab has in it an aperture which can be placed in registration with various backing apertures 56 by movement of the housing tube 6' lengthwise of the backing for correspondingly altering the length of the spring. The tube 6' can be secured to the backing 5' in any desired longitudinally adjusted position by inserting the shank of a headed retaining pin 51 through the aperture in the tube tab and an aperture 56 of the backing 5' in registration with the tab aperture.

In FIG. 50 calibrations 30" on the backing 5' are shown, designating ounces of pull exerted on the side strap 8. The average pull will be indicated by the calibration line in registration with the right end of the housing tube 6'. Such calibration will indicate the exact pull on the side strap 8 when the plunger head 55 is in registration with the zero index mark 31". If the side strap 8 has pulled the plunger head to the right of such index mark, the pull on the side strap will be correspondingly greater than the force indicated by the calibration in registration with the right end of the tube 6', and if the side strap 8 is to the left of the position in which it is seen in FIG. 50, so that the plunger head 55 is at the left of the zero index mark 31", the pull on the side strap 8 will be correspondingly less than the value indicated by the calibration in registration with the right end of the tube 6'.

While the calibration lines 30" are shown in FIG. 50 as cooperating with the right end of the housing tube 6', an additional or alternative type of spring adjustment marking is shown by the numerals 1, 2, 3 and 4 alongside the various apertures 56 of the row of apertures in the backing 5'. Such digital calibrations can be utilized to indicate the various adjusted positions of compression springs 7' having different spring characteristics.

Moreover, the compression spring 7' may be preliminarily stressed so as to produce a substantial force applied to the side strap 8, even when the pin 51 is securing the left end of the tube 6' to the aperture designated 1 of the backing 5'. In such case the extension of the spring 7' is limited by engagement of the shoulder at the junction between the side strap 8 and its reduced portion 8" with the right side of the bridge 12 upstanding from the backing 5'. Such engagement of the shoulder with the bridge will establish one limit of the normal working range of the side strap, and the other limit of such range is reached when the gradually inclined side of the buttress tooth 13b engages the left side of the bridge 12. Further movement of the side strap 8 to the right will pull the buttress tooth beneath the bridge 12 to its right side, effecting latching action of the limit latch formed by bridge 12 and buttress tooth 13b in the manner described in connection with the appliance shown in FIGS. 25 and 26.

In the appliance of FIG. 52, the force applied by the force-producing unit 3" to the side strap 8 is produced by a flat spiral spring 7''', received in a substantially flat casing or housing box 57 carried by the flat backing 5' in parallel relationship. The outer end portion of such spring extends through a slot 58 in such housing and is connected to the reduced extension 8" of the side strap 8 which has a construction similar to that shown in FIGS. 50 and 51. A tab projecting from the side of such casing remote from the slot 58 has in it an aperture that can be placed in registration with any selected one of the aperture 56 arranged in a row lengthwise of the backing 5' to adjust the force produced by the spring 7" and applied to the side strap 8 through the reduced extension 8".

The backing 5' may have calibrations 30" arranged alongside the respective apertures 56 to designate the force which would be produced by the spring 7' and applied to the side strap 8 corresponding to the adjusted position in which the pin 51 secures the casing tab to the backing 5'. While the calibrations are shown as designating ounces of force, the various apertures 56 could simply be designated by digits, as discussed in connection with the appliance shown in FIGS. 50 and 51. The index 31 also cooperates substantially with the end of the spring 7" in a manner similar to that described in connection with FIGS. 5 and 25 to indicate when the spring force being produced corresponds exactly to the calibrations 30. The limit latch structure provided in this appliance is the same as that shown in FIGS. 25, 26, 28, 29, 50 and 51 including cooperating bridge 12 on backing 5' and buttress tooth 13b on strap extension 8".

The embodiment of the invention shown in FIGS. 53 to 58, inclusive, is generally similar to the embodiment shown in FIGS. 25 to 27, inclusive. The force-producing unit 3 includes the helical tension spring 7 received in tube 6 carried by a backing 5.

In this instance the tube is restrained from lateral displacement relative to the backing 5 by being lodged between posts 29" upstanding from the backing at opposite sides of the tube. The free ends of the posts are curved toward each other to restrain movement of the tube away from the backing, but the posts are sufficiently flexible so that their bent ends can be spread to enable the tube to be inserted between the posts by movement transversely of the length of the tube instead of it being necessary to move the tube lengthwise as required to assemble the tube beneath the arch 29' in the construction shown in FIGS. 25 and 26.

The intermediate strap 10 is shorter than such strap shown in FIGS. 25, 26 and 27, because the modification of FIGS. 53 to 57 does not have any limit latch including a buttress tooth 13b, but such limit latch could be provided in this embodiment of the invention if desired. As in the appliance shown in FIGS. 25, 26 and 27, movement of the intermediate strap to the left is limited by engagement of stop rib 19 with the right side of bridge 12".

A main feature of the modified structure shown in FIGS. 53 to 58 is the disconnectible connection between the intermediate strap 10 and the side strap 8'. This connection has the same general type of structure as the connection shown in FIGS. 25, 26 and 27 as including the bridge 18' spanning the end portion of the intermediate strap at the side of stop rib 19 remote from spring 7, which rib cooperates with a reversely-bent spring strip 20',21' carried by the cooperating end of side strap 8'. The principal difference in the two structures is in the proportions of the parts and the manner in which they cooperate.

The structure of the connection shown in FIGS. 53 to 58, inclusive, is very precise, enabling the minimum tension and the amount of movement between side strap 8' and intermediate strap 10 which will effect disconnection of these strap members to be determined quite accurately. In order to be able to select most readily the predetermined minimum tension between strap 8' and strap 10 which will effect disconnection of of the connection, it is preferred that the degree of such tension be determined almost entirely by the characteristics of the spring strip 20', 21'. Consequently, bridge 18' with which such strip cooperates is made of very rigid construction.

The bridge 18' has a deep arch as shown in FIG. 54, and its opposite ends are mounted on the widened end 17 of intermediate strap 10 by upwardly tapered walls 57 forming rigid connections to the intermediate strap end. The rigidity of the widened end of the intermediate strap is also increased by providing sidewalls 58 connecting the opposite ends of the stop rib 19 and the upwardly tapered walls 57 at the opposite ends of the bridge 18'.

The leaf spring 20',21' shown by itself in FIG. 58 is arranged in the connection to utilize both cantilever leaf spring characteristics and semielliptical leaf spring characteristics. The flat base 20' of the spring strip is inserted through a slit in the side strap 8', so that such flat base portion of the spring underlies the underside of the end portion of side strap 8' while the bowed strip portion of the spring lies alongside the other, i.e. upper, face of the side strap. The length of the widened portion 17 of the intermediate strap 10 is shown as being approximately equal to the combined lengths of the spring portions 20' and 21'.

The proportions of the connection parts and the spring characteristics of the spring 20',21' should be quite exact so as to provide a known prestressed condition of the spring when the connector parts have been assembled into the relationship shown in FIGS. 54 and 55. The side strap 8' is assembled with the intermediate strap 10 in the manner described in connection with FIGS. 25, 26 and 27, and illustrated particularly in FIG. 27. In such assembly operation the end of side strap 8' is threaded beneath the bridge 18' and moved from left to right, as seen in FIG. 53, until the assembling operation is completed, with the parts in the positions shown in FIGS. 54 and 55.

During movement of the side strap 8' in the direction indicated by the arrow in FIG. 53 relative to the intermediate strap 10, the bowed portion 21' will engage the bridge 18' before the tip of side strap 8' passes to the right beyond the stop rib 19. In order for the side strap 8' to move relative to the intermediate strap 10 from the position of FIG. 53 to the position of FIGS. 54 and 55, it may be necessary for the cantilever spring characteristics of the spring bow 21' to be overcome completely and such spring bow pressed downward until its free end engages the side strap.

If the side strap 8' is pulled to the right relative to the intermediate strap 10 from the relative positions of these parts shown in FIG. 53, the bridge 18' will apply a wedging force to the right inclined side of the spring bow 21 for depressing such side so that the side strap can continue to be moved to the right. It is preferred that the left end of the cantilever bowed spring leaf 21' be engaged with the upper side of the side strap 8' before such side strap has been pulled far enough to move its tip beyond the right side of the stop rib 19.

The additional movement required before the tip of side strap 8' will snap past the right side of stop rib 19 into the position shown in FIG. 55 should require that the arch of the bowed portion 21' of the spring be depressed to some extent. In such event the spring will be prestressed to the extent of the pull required to bend the bowed portion of the spring into contact with the side strap 8', if the spring is of cantilever type, plus the pull required to depress the arch of the bow spring in order to enable the side strap to move relative to the intermediate strap sufficiently to accomplish such snap action engagement of the parts. The parts will be maintained in such engagement as shown in FIG. 55 thereafter, even though the pull on the side strap 8' is discontinued. Further movement of the side strap to the right relative to the intermediate strap can thereafter be effected only by exerting an extending pull on such straps exceeding the pull required to be exerted in order to assemble the parts to the relationship shown in FIG. 55.

The amount of pull required to be exerted on side strap 8' to displace the side strap relative to the intermediate strap should be greater than the pull exerted on the side strap 8' by spring 7 within the normal working range of the appliance. Thus a pull which will stretch spring 7 from the solid-line position of the intermediate strap 10 to the broken-line position of that figure, in which the shoulder 15' is engaged with the left side of bridge 12", will be insufficient to effect relative extension or separating movement of the side strap 8' and intermediate strap 10. If a pull is exerted on the side strap 8' sufficiently exceeding the pull required to assemble the side strap and the intermediate strap in the relationship shown in FIG. 55 with the spring bow 21' prestressed, the spring bow can be wedged under the bridge 18' and the side strap can move farther to the right relative to the intermediate strap 10, as shown in FIG. 56.

During such further movement of the side strap 8' to the right, the intermediate strap is restrained from being moved by the side strap 8' because of the engagement of shoulder 15' with the left side of bridge 12", as shown in FIG. 56. When the arch of the spring bow 21' has been depressed by wedging action of the bridge 18' to the position shown in FIG. 56, the side strap can be moved easily to the right from the position of FIG. 56 to the position of FIG. 57, in which the side strap 8' is disconnected from the intermediate strap 10.

The extension movement of side strap 8' relative to intermediate strap 10 beyond the position of FIG. 55 to disconnect the straps is very small, such as three to seven millimeters. For the usual orthodontic treatment the pull exerted by spring 7 is in the range of eight to forty-eight ounces, that is, one-half a pound to three pounds. The spring bow 21' may have a preload of four pounds when the parts are in the position shown in FIG. 55, which means that a steady pull of four pounds applied to the side strap 8' will not shift that strap to the right relative to the intermediate strap 10.

The spring 20', 21' may be selected so that a steady pull of five pounds applied to the side strap 8' will move such side strap relative to intermediate strap 10 to and through the position of FIG. 56 to disconnect the connection. A sudden sharp pull of considerably less magnitude could also effect movement of the side strap 8' to the right from the position of FIG. 55 to disconnect the side strap from the intermediate strap. The spring 20', 21' can be selected for disconnection of the parts under loads of different magnitude depending on the type of treatment for which the particular appliance is designed.

The apertures 9' in the side strap 8' of FIG. 54 are larger than the holes 9 in the side strap 8 of the appliance shown in FIGS. 25 to 27, for example, to facilitate connection of such side strap to the hook of the tie rod 2. Also such holes are shown as being numbered for record purposes in fitting the appliance to a particular patient.

FIGS. 59 to 62, inclusive, show a connection component of an orthodontic appliance utilizing a helical compression spring similar to that shown in FIGS. 50 and 51 for producing the force applied to the intraoral component of the appliance. In this unit, the compression spring 7' again is received in the housing tube 6', and the spring right end is seated on an internal flange at the right end of the tube. The side strap 8 has an extension 54' extending axially through the spring and carrying a crosshead 55' engageable with the left end of spring 7'.

The backing 5' has an aperture into which can be inserted the shank of a headed retaining pin 51 secured in a tab projecting from the left end of the tube. The opposite end of the tube is maintained in position centered relative to the backing 5' by posts 28 upstanding from the backing and spaced transversely of the tube to receive the tube end snugly between such posts.

The side strap 8 is connected to the strap section that extends through the spring by a disconnectible connection 151. This disengageable connection is designed to be disconnected when the pull on the side strap 8 exceeds a predetermined value. The orthodontic treating force produced by the spring 7' can, however, be regulated to provide a selected tension value. The effective length of the side strap 8 can be altered by engaging the hook of an outer face bow in different selected holes 9. If a hole is selected to shorten the strap, the strap extension head 55' will be pulled to the right as seen in FIG. 59 to increase the force exerted by the spring. Registration of the crosshead 55 with different calibrations 150 will indicate the amount of force produced by the spring. The calibrations are labeled in ounces so that, if the crosshead 55' is in registration with the index 16, the resilient pull exerted on the intraoral component of the appliance will be 16 ounces.

The disengageable connection between the side strap 8 and the plunger 54' is floating and includes a box 151 in which a return bent leaf spring 152 is received. Such return bent leaf spring includes a lower leg 153 and an upper leg 154 in substantially parallel relationship joined by the return bend 155. Such return bend is hooked through an aperture in the end of strap 8. The portions of legs 153 and 154 adjacent to the return bend extend through an aperture 156 in an end of the box 151 as shown in FIG. 60.

The upper leg 154 of the return bent spring leaf 152 includes an offset 157 that engages the inner side of bridge 18 overlying aperture 156 when the return bent spring is received in the box 151 as shown in FIG. 60. Exertion of a pull on side strap 8 exceeding a predetermined value, such as 7 pounds, for example, will wedge the inclined offset 157 against the bridge 18 with sufficient force to depress the leg 154 from the position shown in FIG. 60 to the position of FIG. 61. The return bent spring 152 will then slide through the aperture 156 to disconnect the connection.

The box and return bent spring of the connection 151 are disconnectible without structural injury and such interfitting elements can again be interfitted in the manner indicated in FIG. 62 to restore the connection shown in FIG. 60. Such reconnection can be accomplished by inserting the end of side strap 8 into the connector box 151 and through the apertures 156 in its end. The strap is then pulled until the return bend 155 passes through the aperture in shown in FIG. 62 and the free end of leg 153 of the return bent spring is resting on the rib 158 forming the end of the box opposite bridge 18. If the outer spring leg 154 is then pressed with the thumb downward and toward the bridge end of the box, the pressure of the offset 157 on the bridge will be relieved so that the leg 153 will slide a short distance to the right and snap easily and quickly down against the bottom 159 of the box, from the position shown in FIG. 62 to the position of FIG. 60. Pressure on the outer leg can then be released and the connection will have been restored for future operation in the manner described above.

The disconnectible disconnection shown in FIG. 63 includes a combination of a connection such as shown in FIGS. 36, 37 and 38 and a compression spring of the type shown in DeWoskin U.S. Pat. No. 3,772,789. The force-producing unit includes a tube 160 from which a force-applying member 161, such as a J-hook, projects. The shank of the J-hook extends axially through a helical compression spring 162 and a ball 87 of a size to seat in the inner end of the compression spring. Withdrawal of the J-hook shank from the ball and spring is prevented by an enlargement 164 on the end of the J-hook shank of greater width than the diameter of the aperture through the bearing ball 163. Such shank end enlargement can be produced simply by flattening the shank end.

The opposite ends of compression spring 162 engage the bearing ball 163 and the right closed end of tube 160. The opposite end of such tube can be connected to a backing 165 by the tube end 166 being flattened and held in flattened condition by a grommet 167 providing an aperture that can be hooked over a hook or staple 168 projecting from the backing 165.

The force-producing unit described is connected to a headgear reaction member 4 by a disconnectible connection such as shown in FIGS. 36, 37 and 38 including a tongue or tail strap 33' that can be inserted beneath a bridge 35 into engagement with a stop rib 34. The backing 165 carries a return bent spring 36 that can be inserted beneath bridge 35 with the tongue or tail strap 33' from the position of FIG. 37 to the position of FIG. 36. By such procedure, a disconnectible connection is established which will be pulled apart to release the force-producing unit from the force-reaction unit when a pull is exerted on the force-applying member 161 exceeding a predetermined value such as approximately 7 pounds of pull, for example.

In FIG. 64 the force-producing component is the same as that shown in FIG. 63. In this instance, however, the backing 105 extend the full length of the spring containing tube 160. The right end of such tube abuts a guide 114 having in it a slot 117 for receiving the shank of the force-applying J-hook 161. The flattened tube end 166 is secured to the backing by a staple or hook 168 upstanding from the backing and engaging the grommet 167 as described previously.

The connection component of FIG. 64 includes a strap or tongue 188 and a socket into which such tongue can be inserted and which will grip the tongue. The socket includes a guide bridge 119 upstanding from the backing 105 beneath which the tongue can be slide freely and a latch bridge 120 spaced lengthwise of the strap and the backing from the guide bridge. Such bridges are integral with the end portion of the backing 105 remote from the guide 114.

The passage beneath guide bridge 119 is deeper than the greatest thickness of tongue 118. Such tongue is not of uniform thickness, but its outer surface has a row of parallel grooves 121 extending transversely of the length of the tongue and spaced lengthwise of it. Intervals between such grooves are selected to correspond to the increments by which it is desired to be able to adjust the effective length of the connection between the force-producing unit backing 105 and the force-reaction means 128.

Each tongue 121 is of trapezoidal cross section including a steeply inclined or abrupt wall nearer the tip 125 of the tongue and a gradually sloping wall farther from the tongue tip. The abrupt buttress wall may be at an angle of approximately 120° to the flat bottom of the groove and the gradually sloping wall may be at an angle of approximately 150° relative to the flat bottom of the groove so that such groove walls are mutually perpendicular. The spaced grooves in one side of the tongue 118 form buttress lands or teeth 124 between such grooves which constitute linear ratchet teeth. The height of the passage beneath latch bridge 120 when the bridge is in relaxed condition is less than the greatest thickness of the lands or teeth of the strap or tongue 118. The tip 125 of the tongue is double beveled to guide movement of such tip beneath the guide bridge 119 and the latch bridge 120.

When the tongue 118 is pushed relative to the force-producing unit backing 105 to the right, as seen in FIG. 64, the tip of the tongue will first slide readily beneath the guide bridge 119 and the wedge-shaped tongue tip 125 will move beneath the latch bridge 120. If the tongue is then pushed with greater force, the outer bevel of the wedge-shaped end 125 will deflect the bridge 120 outwardly sufficiently so that the leading land 124 of the tongue will pass beneath the latch bridge.

The width of the latch bridge is preferably slightly narrower than the maximum width of the tongue groove 121 so that when the tongue has been pushed to the position shown in FIG. 64, the bridge will be in registration with a groove 122 and will be relaxed from its set position. Preferably, there is little or no backlash between the tongue and bridge. The tongue 18 can be pushed relative to the latch bridge to the right until the tongue comes into registration with any successive groove which is appropriate to establish the desired length of the connection between the force-producing unit and the force-reaction member 128.

In use, the tongue 118 is moved into the socket formed by the bridges 119 and 120 until the desired relationship between the force-producing unit and the force-reaction member is established. By selecting the proper length of connection, the headgear can be fitted to various patients by using the same size of force-producing unit and the same size of head-engaging member or neck-engaging member, or at least by providing a smaller selection of sizes than would be necessary if the connector were not adjustable in effective length by altering the setting of the linear ratchet formed by the connector strap tongue 118 and latch bridge 120.

The position of the tongue 118 relative to the latch bridge 120 is set both with reference to the size of the patient's head and with reference to the degree of pull desired to be transferred by the force-producing unit to the force-applying member 161. The force produced by the force-producing unit can be increased simply by shortening the connection effected by the tongue and latch bridge. The spacing between adjacent grooves 121 corresponds to predetermined changes in the force increment produced by the spring 162.

When a pull between the force-reaction member 128 and the force-applying member 161 exceeds a predetermined value, the tongue 118 will be pulled out of the socket formed by the bridges 119 and 120. Consequently, it is desirable for the latch bridge to be in engagement with the groove of the tongue nearest its tip 125 when the headgear is in operation. After the desired adjusted relationship between the tongue and the force-producing unit has been established, therefore, any portion of the strap or tongue 118 projecting beyond the side of the latch bridge 120 remote from the guide bridge 119 should be cut off through the bottom of the groove adjacent to that side of the latch bridge.

The connection component shown in FIGS. 65 and 66 includes a force-producing unit similar to that shown in FIGS. 63 and 64, but in this instance the connection between the force-producing unit and the force-applying component is a side strap 8 similar to that shown in FIG. 59, instead of being a J-hook 161 as shown in FIGS. 63 and 64. In this instance the side strap 8 has elongated apertures 9' spaced along its length for engagement with a hook in the outer end of an outer face bow. The end of tube 169 enclosing the compression spring has in it a slot 170 through which the end portion 54' of the sidestrap 8 can pass. The end portion of the sidestrap extends axially through the compression spring 162, and an enlargement 55' on the end of the strap is engageable with the end of the compression spring remote from the tube end aperture 170 to transmit force between the sidestrap 8 and the spring.

The tube 169 has numbered calibrations 171 marked on it to indicate the degree of compression of spring 162, and consequently the amount of force produced by the spring on the sidestrap 8 which is transmitted to the face bow.

The end of spring housing tube 169 remote from its apertured end 170 is secured to a force-reaction extraoral component 4 including a disconnectible connection of the type described in connection with FIG. 63. The backing 165 carries a hook or staple 168 engageable by the grommet 167 inserted in the flattened end 166 of the tube 169. A return bent spring is inserted through tongue 33' of the backing, and such return bent spring can be inserted beneath bridge 35 on the reaction member 34 until tongue 33' engages the stop rib 34 to form the disconnectible connection.

The connector component shown in FIG. 67 includes a compression spring force-producing unit similar to that of FIGS. 65 and 66 and a disconnectible connector like that shown in FIG. 64. The end of compression spring housing tube 169 having the end aperture 170 from which the sidestrap 8 projects is held against lateral movement by posts 28 projecting outward from backing 5" as described in connection with FIGS. 23 and 59. In addition, the spring housing tube can be held to the backing 5" by being lodged between posts 29" upstanding from the backing 5" at opposite sides of the central portion of the tube. The free ends of these posts are curved toward each other to restrain movement of the tube away from the backing, but the posts are sufficiently flexible so that their bent ends can be spread to enable the tube to be inserted between the posts by movement transversely of the length of the tube, instead of it being necessary to thread the tube lengthwise between the posts.

The disengageable connection including tongue 118 having a transverse notch 121 and rib 124 receivable beneath bridges 119 and 120 has been described in connection with FIG. 64.

The connector component of FIGS. 68 and 69 includes both a limit latch and two disconnectible connectors. The compression spring 7' and its housing 169 are similar to those described in connection with FIG. 67. The backing 172 can be adjustably connected to the flattened end 173 of tube 169 remote from limit latch bridge 12" by a selected one of apertures 174 arranged in a row along the flattened tube end being engaged with a hook or hooked staple end 175 carried by the backing 172. The force produced by the spring in various adjusted positions of the tube 169 is indicated by the right end of such tube being in registration with one of the calibration marks 30 when the crosshead 55' is in registration with the zero calibration.

The force-producing unit can be connected to the force-reaction member 4 by a disconnectible connection including tongue 176 inserted beneath bridge 135 upstanding from the force-reaction component and into a housing 177 upstanding from such component. This disconnectible connection is similar to the connection shown in FIG. 34 including a buttress tooth 32 molded integrally with the tongue or tail strap 176. The side of the buttress tooth 32 nearer bridge 35 is more abrupt than the opposite side, and the tooth is of a height to snap beneath the bridge 35 as the tail strap or tongue is pulled to the right with a force that exceeds a predetermined value. Excessive pull beyond such predetermined value will cause the abrupt side of the tooth or buttress member 32 to wedge the bridge 35 outward and disconnect the connection afforded by the tooth 32 engaging the left side of the bridge 35.

In addition, the connection component can have both a limit latch and a disconnectible connection between the force-producing unit and the sidestrap 8 that transmits force to the intraoral face-applying component. Such construction includes a limit latch similar to that shown in FIGS. 25 to 29 and 33 and a disengageable connection similar to that shown in FIG. 33. Instead of having a considerable number of buttress teeth integral with the sidestrap as in FIG. 33, however, the construction of FIGS. 68 and 69 includes only two buttress teeth 32 that can be disposed at opposite sides of the bridge 18, respectively, in conjunction with a sidestrap having perforations 9 like the sidestrap in FIGS. 5 to 14 and 59, for example.

The operation of the limit latch, including tooth 13b molded integrally with the intermediate strap 10, which cooperates with the bridge 12", is similar to that described in connection with FIGS. 25 to 29, inclusive. Preferably the tooth 13b and the intermediate strap 10 are molded of plastic material. The inclined or sloping side of the buttress tooth or wedging member 13b will engage the left side of the latch bridge 12". Such buttress tooth and/or the bridge will be sufficiently yieldable to enable the buttress tooth to be pulled beneath the bridge when a force of predetermined maximum value is applied to the sidestrap 8 and to the force-producing unit 3 tending to separate them.

When the buttress tooth 13b has been pulled beneath the bridge 12" to the side opposite that shown in FIG.

69, the force of the spring 7' will be insufficient to pull the abrupt or sheer side of such tooth back under the bridge. The buttress tooth 13b can, however, be moved manually at will back under the bridge 12" from the latched position by direct manual lengthwise pressure on the intermediate strap, or by swinging the intermediate strap relative to the bridge as shown in FIG. 29.

The disconnectible connection between the sidestrap 8 and the intermediate strap 10 includes buttress teeth 32 molded integrally with the sidestrap 8. These buttress teeth are of a height to snap successively beneath the bridge 18 as the strip is pulled to the right relative to the intermediate strap 10. When the pull on the sidestrap exceeds a predetermined value, the buttress tooth engaging the left side of the bridge 18 will wedge the bridge outward and be pulled beneath the bridge to disconnect the connection between the intraoral component to which the sidestrap 8 is connected and the force-producing unit including the spring 7'. Such connection can be restored by threading the strap 8 beneath the bridge again from left to right to the position of FIGS. 68 and 69.

I claim:

1. In an orthodontic appliance including force-reaction means, orthodontic force-applying means and a resilient connection connecting the force-reaction means and the force-applying means and having a resilient force-producing unit, the improvement comprising a disengageable connection connected to the resilient force-producing unit and having interengageable elements disconnectible without structural injury by movement of the force-reaction means and the orthodontic force-applying means away from each other exceeding a predetermined distance, said interengageable elements when disconnected being again interengageable to restore the same connection, and the resilient force-producing unit including helical compression spring means.

2. In the orthodontic appliance defined in claim 1, the disengageable connection being connected between the resilient force-producing unit and the force-reaction means.

3. In the orthodontic appliance defined in claim 1, the disengageable connection being connected between the resilient force-producing unit and the orthodontic force-applying means.

4. In the orthodontic appliance defined in claim 1, the interengageable elements being of plastic material and at least one of such elements being yieldable for disconnection of the interengageable elements.

5. In the orthodontic appliance defined in claim 1, one of the interengageable elements being a bridge of plastic material and the other element being a return bent metal spring.

6. In the orthodontic appliance defined in claim 5, the return bent metal spring including two substantially straight parallel legs, except that one of said legs includes an offset engageable with the bridge.

7. In an extraoral orthodontic appliance, a disconnectible connection including a bridge and a resilient member engageable with and movable beneath said bridge for disconnection of said bridge and said resilient member, said resilient member being a return bent metal spring including substantially straight parallel legs, except that one of said legs has an offset engageable with said bridge.

8. In the connection defined in claim 7, the portion of the return bent spring leg having the offset which portion is at the side of the offset remote from the return bend of the spring being substantially straight and parallel to the other leg of the return bent spring when the offset is in engagement with the bridge.

9. In the connection defined in claim 7, the free end of the portion of the leg having the offset which portion is at the side of such offset remote from the return bend being at least substantially as far from the other leg of the return bent spring as the offset is from such other leg when the offset is engaged with the bridge.

10. In an orthodontic appliance including force-reaction means engageable with the wearer's head and/or neck, orthodontic force-applying means for applying force to a jaw and resilient force-producing means connecting the force-reaction means and the force-applying means for exerting a force tending to reduce the distance between such two connected means, the force-reaction means, the force-producing means and the force-applying means cooperatively forming a ring for encircling the wearer's head, the improvement comprising the ring including a safety connection having cooperating parts automatically operable by an external force greater than a predetermined force acting on the ring in opposition to the force produced by the resilient force-producing means, said connection cooperating parts being operated by such external force to relieve the force-applying means from force produced by the force-producing means which would be capable of moving the force-applying means an appreciable distance toward the wearer's face after action of such external force on the ring, and the force-producing means including helical compression spring means.

* * * * *